(12) United States Patent
Parthasarathy et al.

(10) Patent No.: US 10,639,021 B2
(45) Date of Patent: May 5, 2020

(54) SHAPEABLE ARTICLES AND METHODS OF MAKING AND USING THE SAME

(71) Applicant: 3M INNOVATIVE PROPERTIES COMPANY, Saint Paul, MN (US)

(72) Inventors: Ranjani V. Parthasarathy, Woodbury, MN (US); Hannah C. Cohen, Saint Paul, MN (US); Haoming Rong, Woodbury, MN (US); Amanda C. Engler, Woodbury, MN (US); William Bedingham, Woodbury, MN (US); Nicholas R. Powley, Saint Paul, MN (US); Korey W. Karls, Woodbury, MN (US); Michael J. Vostal, Minneapolis, MN (US); Matthew T. Scholz, Woodbury, MN (US); Michelle H. Stevens, Bloomington, MN (US); Catherine D. Heapy, North Saint Paul, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 16/345,231

(22) PCT Filed: Oct. 23, 2017

(86) PCT No.: PCT/US2017/057819
§ 371 (c)(1),
(2) Date: Apr. 25, 2019

(87) PCT Pub. No.: WO2018/085067
PCT Pub. Date: May 11, 2018

(65) Prior Publication Data
US 2019/0290252 A1 Sep. 26, 2019

Related U.S. Application Data

(60) Provisional application No. 62/417,108, filed on Nov. 3, 2016.

(51) Int. Cl.
*A61B 17/02* (2006.01)
*B32B 7/05* (2019.01)
(Continued)

(52) U.S. Cl.
CPC .............. *A61B 17/02* (2013.01); *B32B 3/28* (2013.01); *B32B 7/05* (2019.01); *B32B 15/00* (2013.01);
(Continued)

(58) Field of Classification Search
CPC ... A61B 17/02; A61B 17/0231; A61B 17/025; A61B 17/0218; A61B 2017/0212;
(Continued)

(56) References Cited

U.S. PATENT DOCUMENTS 1,944,009 A   1/1934   Homer
3,813,148 A   5/1974   Kraus
(Continued)

FOREIGN PATENT DOCUMENTS

EP    0267640       5/1988
WO    WO 2016/100174    6/2016
(Continued)

OTHER PUBLICATIONS

"Volara Type EO—Volara® Technical Data", A Technical Data Sheet from Sekisui Voltek, Lawrence Massachusetts, Jan. 2010; 2 pages.
(Continued)

*Primary Examiner* — Ellen C Hammond
(74) *Attorney, Agent, or Firm* — 3M Innovative Properties Company; Jonathan V. Sry

(57) ABSTRACT

Shapeable articles, kits including one or more of the shapeable articles, and methods of making and/or using the shapeable articles. The shapeable articles include a shapeable member that can be shaped or manipulated into three-
(Continued)

dimensional shapes without the use of tools and hold those shapes after removal of the force required to achieve the shape. The shapeable articles could have a variety of uses including use as surgical retractors to move and/or restrain non-target tissue and/or organs to improve access to the target tissue and/or organs.

15 Claims, 17 Drawing Sheets

(51) Int. Cl.
*B32B 3/28* (2006.01)
*B32B 15/20* (2006.01)
*B32B 15/00* (2006.01)
*A61B 17/00* (2006.01)

(52) U.S. Cl.
CPC .... *B32B 15/20* (2013.01); *A61B 2017/00526* (2013.01); *A61B 2017/00858* (2013.01); *A61B 2017/00871* (2013.01); *A61B 2017/00946* (2013.01); *A61B 2017/00964* (2013.01); *A61B 2017/0225* (2013.01); *B32B 2535/00* (2013.01)

(58) Field of Classification Search
CPC .... A61B 2017/0225; A61B 2017/0256; A61B 2017/0268; A61B 2017/0275; A61B 2017/00946; B32B 7/05; B32B 3/28
See application file for complete search history.

(56) References Cited

U.S. PATENT DOCUMENTS

| | | |
|---|---|---|
| 4,533,356 A | 8/1985 | Bengmark |
| 4,889,107 A | 12/1989 | Kaufman |
| 5,007,418 A | 4/1991 | Bartizal |
| 5,171,041 A | 12/1992 | McMillan |
| 8,080,304 B2 | 12/2011 | Clarke |
| 8,529,444 B2 | 9/2013 | Hale |
| 2007/0066186 A1* | 3/2007 | Annen ............... B24D 3/32 451/41 |
| 2010/0087713 A1 | 4/2010 | Eliash |
| 2012/0316430 A1 | 12/2012 | Aldag |
| 2013/0291399 A1 | 11/2013 | Fonte |

FOREIGN PATENT DOCUMENTS

| | | |
|---|---|---|
| WO | WO 2018-085066 | 5/2018 |
| WO | WO 2018-085068 | 5/2018 |
| WO | WO 2018-098803 | 6/2018 |
| WO | WO 2018-111668 | 6/2018 |
| WO | WO 2019-064120 | 4/2019 |
| WO | WO 2019-064121 | 4/2019 |

OTHER PUBLICATIONS

International Search Report for PCT International Application No. PCT/US2017/057821, dated Apr. 12, 2018, 8 pages.
International Search Report for PCT/US2017/057819 dated Apr. 9, 2018.

* cited by examiner

SHAPEABLE ARTICLES AND METHODS OF MAKING AND USING THE SAME

CROSS REFERENCE TO RELATED APPLICATIONS

This application is a national stage filing under 35 U.S.C. 371 of PCT/US2017/057819, filed Oct. 23, 2017, which claims the benefit of U.S. Provisional Application No. 62/417,108, filed Nov. 3, 2016, the disclosure of which is incorporated by reference in its entirety herein.

FIELD OF THE INVENTION

This invention generally relates to shapeable articles, kits incorporating the same and methods of making and/or using the articles.

BACKGROUND

The restraint of tissues and organs during surgical procedures allows for access and/or visualization of the target tissues and organs that are the focus of the surgical procedures. Although rigid retraction devices and apparatus may be used in some surgical procedures, e.g., the BOOKWALTER retractor system, such retractors may be the source of damage to retracted tissues and/or organs. The potential damage is significant because, for example, there are approximately 1.4 million open abdominal surgeries every year in the United States. About 8.5% of those surgeries lead to ileus, which is a cessation of bowel function. Ileus results in nausea, vomiting, bloating, pain, extended hospital stays, and $1.46 billion increased cost for common abdominal procedures. Additionally, peritoneal adhesions can be found in up to 93% of patients undergoing intra-abdominal surgery.

Attempts to provide malleable or shapeable pads that can be used to restrain tissues and/or organs during surgical procedures are described in, e.g., U.S. Patent Application Publication No. US 2010/0087713. The approaches described in that document do not, however, fully appreciate the issues or solve the problems associated with tissues/organ restraint during surgical procedures.

SUMMARY

The present invention is directed to shapeable articles, kits including one or more of the shapeable articles, and methods of making and/or using the shapeable articles. Although the shapeable articles could have a variety of uses, one use for which they may be well-suited is as surgical retractors used in surgery to move and/or restrain non-target tissue and/or organs to improve access to the target tissue and/or organs.

The shapeable articles described herein can be shaped or manipulated into three-dimensional shapes without the use of tools and hold those shapes after removal of the force required to achieve the shape. In other words, "shapeable" (and variations thereof) as used herein means that an article or component may be plastically deformed from an original shape such that the article or component takes and maintains a selected shape after forming and, further, the shapeable article or component can be further manipulated to return to a configuration that is the same or nearly the same as its original shape. In one or more embodiments, the shapeable articles described herein incorporate one or more ductile metals to provide the required deformation and shapeability.

When used in surgical procedures, the shapeable articles may be used alone or in conjunction with other retraction apparatus (e.g., table-mounted retraction systems such as, e.g., BOOKWALTER retractor systems, etc.). Whether used alone or with other retraction apparatus, the shapeable articles may be manipulated to take a desired shape to assist in the restraint of tissues and/or organs during a surgical procedure.

The shapeable articles may provide one or more advantages when used in surgical procedures. For example, in one or more embodiments, the shapeable articles described herein may preferably improve the uniformity of pressure distribution over the surface of the shapeable article, limit or prevent tissue impingement (e.g., "pinching," etc.), limit unnecessary tissue/organ movement such as tissues/organs slipping out from behind a shapeable article/retractor, and/or reduce the occurrence of pressure points—any one of which may cause tissue or organ damage during a surgical procedure. For example, excessive pressure on tissue can cause damage to that tissue. One manner in which one or more embodiments of the shapeable articles described herein may reduce pressure points is by limiting or even, in one or more embodiments, preventing the formation of creases caused by manipulation of the shapeable article.

Control over bending of the shapeable members of one or more embodiments of shapeable articles as described herein can play a role in reducing pressure points that may be exerted on tissue/organs by the shapeable articles described herein. In particular, creases can be expected to form pressure points (i.e., local areas of increased pressure) when the shapeable articles described herein contact tissue/organs. As a result, reducing the likelihood and/or prominence of creases can play a role in reducing the likelihood of pressure points when using the shapeable articles described herein to restrain tissues/organs.

In one or more embodiments, the shapeable members may bend along lines that follow paths that extend between structured elements of the shapeable members (e.g., land portions as described in connection with one or more embodiments of the shapeable articles described herein). Further, the structured elements may, in one or more embodiments, control or limit the radius of curvature which may also limit creasing of the shapeable members of shapeable articles as described herein.

That same control over bending paths during deformation from a flat to a non-flat configuration may also, in one or more embodiments, control bending of the shapeable members of shapeable articles as described herein when the shapeable articles are being manipulated in attempt to return to their flat configuration before being bent. In other words, control over the bending of a shapeable article from a flat configuration to a bent configuration may also control bending of the shapeable article when being manipulated to return to a flat (or near-flat) configuration after having been bent. That control over bending may, in one or more embodiments, reduce creasing of the shapeable articles. Reduced creasing may, as discussed herein, reduce pressure points and resulting tissue/organ injury when using the shapeable articles described herein to restrain tissue/organs.

Another potential advantage of one or more embodiments of the shapeable articles, when adapted for use in surgical procedures as described herein, may be found in a reduction in surface abrasion of tissues and/or organs that come into contact with the shapeable articles. In one or more embodiments of the shapeable articles as described herein, the outer surfaces of the shapeable articles may have a coefficient of friction within a selected range that is high enough (even when wet) to assist in retention of tissues and/or organs, but is low enough such that excessive abrasion of tissues and organs is significantly reduced during use of the shapeable articles.

In a first aspect, one or more embodiments of the manually shapeable articles as described herein may include: a shapeable member comprising a first sheet comprising a first major surface and a second major surface, wherein the first major surface and the second major surface are on opposite sides of the first sheet, wherein the first sheet further comprises a land portion extending between and connecting a plurality of structured elements, wherein each structured element of the plurality of structured elements comprises a protrusion extending from the land portion on the first major surface of the first sheet. The shapeable member may also optionally include a second sheet comprising a first major surface and a second major surface, wherein the first major surface and the second major surface are on opposite sides of the second sheet, wherein the second sheet further comprises a land portion extending between and connecting a plurality of structured elements, wherein each structured element of the plurality of structured elements comprises a protrusion extending from the land portion on the first major surface of the second sheet; wherein the first sheet is attached the second sheet such that the second major surface of the first sheet faces the first or second major surface of the second sheet. A first coversheet is attached to a first major surface of the shapeable member; and a second coversheet is attached to a second major surface of the shapeable member.

In a second aspect, one or more embodiments of a manually shapeable surgical retractor as described herein may include: a shapeable member comprising a malleable core, wherein the shapeable member comprises a first major surface and a second major surface, wherein the first major surface and the second major surface are on opposite sides of the shapeable member and the malleable core; a first coversheet attached to a first major surface of the shapeable member; and a second coversheet attached to a second major surface of the shapeable member; wherein the surgical retractor comprises a perimeter in the general shape of a rectangle, with one or more tabs extending outward from at least one side of the rectangular, wherein each tab of the one or more tabs occupies less than all of the side from which it extends. In one or more embodiments, the shapeable member extends into the area defined the one or more tabs.

In a third aspect, one or more embodiments of a manually shapeable surgical retractor as described herein may include: a shapeable member comprising a malleable core, wherein the shapeable member comprises a first major surface and a second major surface, wherein the first major surface and the second major surface are on opposite sides of the shapeable member and the malleable core; a first coversheet attached to a first major surface of the shapeable member; and a second coversheet attached to a second major surface of the shapeable member; wherein the surgical retractor comprises non-rectangular shape comprising a central portion and two or more fingers extending outwardly from the central portion, wherein the shapeable member extends into each finger of the two or more fingers.

In a fourth aspect, one or more embodiments of a manually shapeable surgical retractor as described herein may include: a shapeable member comprising a malleable core, wherein the shapeable member comprises a first major surface and a second major surface, wherein the first major surface and the second major surface are on opposite sides of the shapeable member and the malleable core; a first coversheet attached to a first major surface of the shapeable member; and a second coversheet attached to a second major surface of the shapeable member; wherein the first coversheet and the second coversheet define a surgical retractor perimeter having a retractor shape, and wherein the shapeable member located between the first coversheet and the second coversheet comprises a member perimeter defining a member shape that is different than the retractor shape.

In a fifth aspect, one or more embodiments of a manually shapeable surgical retractor as described herein may include: a shapeable member comprising a malleable core, wherein the shapeable member comprises a first major surface and a second major surface, wherein the first major surface and the second major surface are on opposite sides of the shapeable member and the malleable core; a first coversheet attached to a first major surface of the shapeable member; and a second coversheet attached to a second major surface of the shapeable member; wherein the first coversheet and the second coversheet define a surgical retractor perimeter having a retractor shape, and wherein the shapeable member located between the first coversheet and the second coversheet comprises a member perimeter defining a member shape that is the same as the retractor shape.

In a sixth aspect, one or more embodiments of a manually shapeable surgical retractor as described herein may include: a shapeable member comprising a malleable core, wherein the shapeable member comprises a first major surface and a second major surface, wherein the first major surface and the second major surface are on opposite sides of the shapeable member and the malleable core; a first coversheet attached to a first major surface of the shapeable member; and a second coversheet attached to a second major surface of the shapeable member; wherein the first coversheet and the second coversheet define an article perimeter having a generally rectangular shape, and wherein the shapeable member located between the first coversheet and the second coversheet comprises a member perimeter defining a non-rectangular member shape that is different than the generally rectangular shape of the article perimeter. In one or more embodiments, the non-rectangular member shape comprises a generally rectangular shape comprising one or more tabs extending outward from at least one side of the rectangular, wherein each tab of the one or more tabs occupies less than all of the side from which it extends.

In a seventh aspect, one or more embodiments of a kit as described herein may include a lap sponge in one or more surgical retractors in the form of manually shapeable articles as described herein. The components of the kit may be contained within a frangible sealed package.

The above summary is not intended to describe each embodiment or every implementation of the articles, kits, and/or methods as described herein. Rather, a more complete understanding of the invention will become apparent and appreciated by reference to the following Detailed Description and claims in view of the accompanying figures of the drawing.

BRIEF DESCRIPTIONS OF THE DRAWING

DETAILED DESCRIPTION

Figure 1:
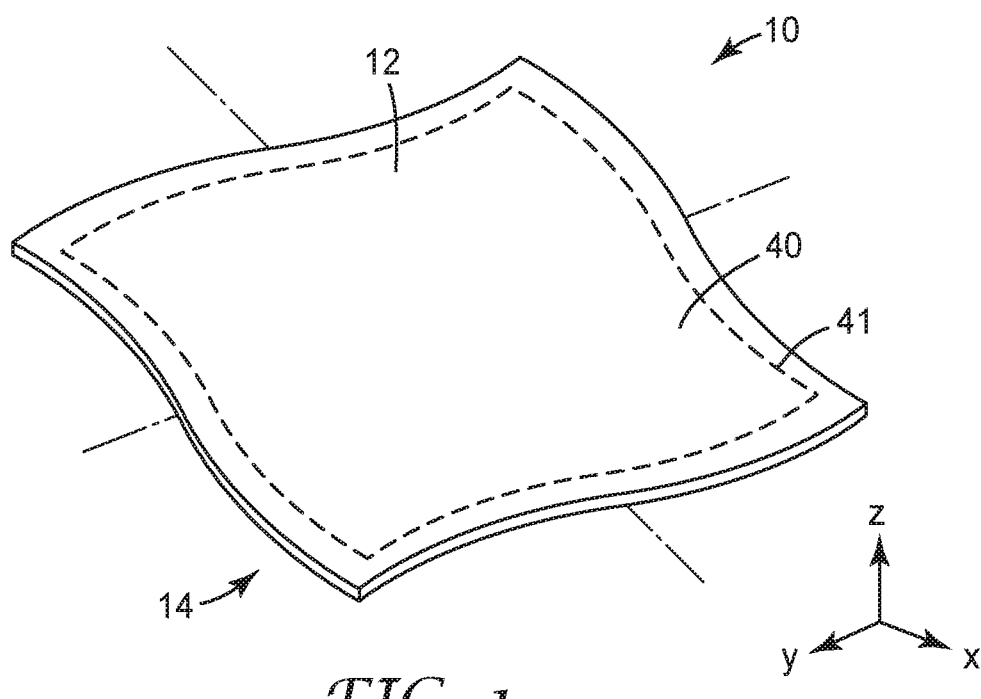
FIG. 1 is a perspective view of one illustrative embodiment of a shapeable article as described herein.

In the following description, reference is made to the accompanying figures of the drawing which form a part hereof, and in which are shown, by way of illustration, specific embodiments. It is to be understood that other embodiments may be utilized and changes may be made without departing from the scope of the present invention.

Although described in terms of their use in surgical procedures, the shapeable articles described herein may find many uses in other applications as well, and description of the illustrative embodiments in a surgical setting should not be construed as limiting the use of shapeable articles constructed according to the principles described herein to surgical procedures.

One illustrative embodiment of a shapeable article 10 as described herein is depicted in FIG. 1. The shapeable article 10 includes two major surfaces 12 and 14 located on opposite sides of the shapeable article 10 which is provided in the form of a sheet or pad. Although the shapeable article 10 can take a flat configuration in which the two major surfaces 12 and 14 are essentially planar surfaces, the shapeable articles 10 as described herein can be manipulated into non-planar configurations. In other words, although the shapeable articles 10 can be provided in a configuration in which the surfaces 12 and 14 essentially lie in an X-Y plane with the thickness of the shapeable article 10 extending in a Z direction, the shapeable articles 10 can be manipulated such that the first and second major surfaces 12 and 14 no longer lie in a plane, e.g., are curved or otherwise non-planar. In one or more embodiments, however, the manipulation does not substantially change the thickness of the shapeable article 10 between its first and second major surfaces 12 and 14. Rather, the shapeable articles 10 form complementary curves on major surfaces 12 and 14.

The shapeable article 10 in FIG. 1 is depicted after manipulation from a flat planar configuration such that first major surface 12 exhibits a combination of convex and concave surfaces while the second major surface 14 also exhibits a combination of convex and concave surfaces that are the opposite of those found on first major surface 12. In other words, where first major surface 12 exhibits a convex surface, second major surface 14 exhibits a complementary concave surface and vice versa. The X, Y and Z axes of a representative Cartesian coordinate system depicted in FIG. 1 may be included in figures where helpful to provide a frame of reference when describing the shapeable articles and methods described herein.

As discussed above, the shapeable articles described herein can be shaped or manipulated into three-dimensional shapes without the use of tools and hold those shapes after removal of the force required to achieve the shape. In those embodiments in which the shapeable articles are to be manually formed into a desired shape or configuration, it may be beneficial to limit the force needed to bend or form the shapeable articles. In one or more embodiments, the shapeable articles as described herein may be defined in terms of stiffness. In particular, in one or more embodiments, the shapeable articles described herein may have a stiffness allowing for manual deformation of the shapeable articles into desired shapes without requiring tools to do so. In one or more embodiments, the shapeable articles as described herein may have a stiffness of 100N or less, 80N or less, 60N or less, 40N or less, 20N or less, or even 10N or less as measured using a Three-Point Bend test. In other words, bending of the shapeable article 10 around either of the axes depicted in FIG. 1 may, in one or more embodiments, require a force of 100N or less, 80N or less, 60N or less, 40N or less, 20N or less, or even 10N or less according to the identified test method.

In addition to being manually deformable into one or more selected shapes as described herein, one or more embodiments of the shapeable articles described herein exhibit limited elastic recovery after being deformed. For example, in one or more embodiments, the shapeable articles described herein recover 20% or less (or in one or more alternative embodiments, 10% or less) of any deflection imparted to them during deformation after a period of 5 minutes or less (or, in one or more embodiments, 2 minutes or less) after removal of the force applied to deform the shapeable article. In one or more embodiments of the shapeable articles described herein, the shapeable articles may exhibit little or no elastic recovery (e.g., have an elastic recovery of 0% or more) of any deflection imparted to them during deformation within the time periods described above.

The shapeable articles described herein are constructed of multiple components attached together to form a shapeable article such as shapeable article 10 depicted in FIG. 1. One illustrative embodiment of components that may be included in shapeable articles as described herein are depicted in the exploded diagram of FIG. 2. The depicted shapeable article 10 includes a first coversheet 20, second coversheet 30, and shapeable member 40 attached together to form the shapeable article 10. The first coversheet 20 can be attached to a first major surface of the shapeable member 40 while the second coversheet 30 is attached to a second major surface of the shapeable member 40. The first and second major surfaces of the shapeable member 40 are, like the major surfaces 12 and 14 of the shapeable article 10, located on opposite sides of the shapeable member 40.

In one or more embodiments, the first coversheet 20 may be attached to the shapeable member 40 and/or to the second coversheet 30 on the opposite side of the shapeable member 40 using adhesive 28. Similarly, the second coversheet 30 may, in one or more embodiments, may be attached to the shapeable member 40 and/or to the first coversheet 20 using adhesive 38. In one or more embodiments, the first coversheet 20 may be described as being attached to the second coversheet 30 about a perimeter of the shapeable member 40. As seen in, e.g., FIG. 1, the perimeter 41 of the shapeable member 40 is inset from the perimeter of the coversheets and, in such an embodiment, the first and second coversheets 20 and 30 may be attached to each other about the perimeter of the shapeable member 40. The shapeable member 40 itself may be attached to the first and second coversheets 20 and 30 using any suitable technique, e.g., adhesives, welding (one or more of thermal, chemical, and mechanical welding), sewing, mechanical fasteners (e.g., hook and loop fasteners, stem fasteners (e.g., 3M DUAL LOCK reclosable stem fasteners), etc.), riveting, stitching, crimping, etc. over any necessary portion of the perimeter to maintain the components in position with each other. Further, although adhesives 28 and 38 are depicted as being continuous layers in FIG. 2, the adhesives 28 and 38 used to attach coversheets 20 and 30 to each other and/or to a shapeable member 40 may be continuous or discontinuous (e.g., pattern coated, etc.). One or both of the adhesives 28 and 38 may, in one or more embodiments, be a pressure sensitive adhesive such as, e.g., an acrylate, polyurethane, polyolefin, styrene copolymer or a combination thereof; a hot melt adhesive such as a polyolefin or modified polyolefin (ethylene vinylacetate, ethylene acrylates such as ethylene methylacrylate, acrylates such as KURARITY (from Kuraray) and the like), or a curable adhesive such a 2 part silicone, epoxy, or polyurethane.

Although adhesives are used in constructing one or more embodiments of the shapeable articles 10 as described herein, coversheets may be attached to each other and/or the shapeable member 40 of a shapeable article 10 as described herein through the use of other techniques such as, e.g., insert molding, etc. If insert molding is used, the first and second coversheets may not be separately discernible layers/components around the perimeter of the shapeable member 40 because the material used for the coversheets may form a contiguous mass about the perimeter 41 of the shapeable member 40. In still other alternative embodiments, the first and second coversheets may be chemically or thermally welded to each other about the perimeter 41 of the shapeable member 40.

The first coversheet 20 and second coversheet 30 on a shapeable article as described herein may be constructed of the same or different components depending on the intended use of the shapeable articles described herein. When intended for use in surgical procedures, the first and second coversheets 20 and 30 may include a variety of different components configured to assist in restraining tissue and/or organs while reducing trauma due to, e.g., pressure points, abrasion, etc.

In one or more embodiments, the coversheets used in shapeable articles described herein may include one or more components such as, e.g., foam layers, polymeric films/sheets, nonwoven sheets, woven sheets, knitted sheets, mesh sheets, net sheets, etc. Further, a coversheet as used in connection with the shapeable articles described herein may include two or more different layers of the same material, e.g., a single coversheet may include two foam layers, two polymeric film/sheet layers, etc. Further, one or more layers of any coversheet used in one or more embodiments of the shapeable articles as described herein may be absorbent such that the layer or layers absorb water, normal saline, etc. before or during use as desired. Still further, one or more layers of any coversheet used in one or more embodiments of the shapeable articles as described herein may be nonabsorbent such that the layer or layers do not absorb water, normal saline, etc. before or during use as desired.

In one or more embodiments in which a coversheet used on a shapeable article as described herein includes a compressible layer to, e.g., control the formation of pressure points on tissue and/or organs that come into contact with the shapeable article. Examples of some potentially suitable compressible layers that may be used in connection with one or more embodiments of the shapeable articles described herein may include open or closed cell foams, silicone sheets, polyurethanes, silicone polyureas, silicones, cotton, polyesters, ethylene vinyl acetate, etc.

In one or more embodiments, a compressible coversheet used in a shapeable article as described herein may exhibit compression set of 50% or less (or, alternatively, 30% or less or even 20% or less) of an original thickness when tested according to ASTM D3575. In one or more embodiments, a compressible coversheet used in a shapeable article as described herein may be in the form of a sheet of closed cell EVA copolymer foam, one potentially suitable version of which is available from Sekisui Voltek, Lawrence Mass., USA under the designation VOLARA Type EO with a density of 3.2 kilograms per cubic meter (e.g., 2 pounds per cubic foot) and a thickness of 1.57 mm (e.g., 0.062 inches).

In one or more embodiments of the shapeable articles described herein, one or both of the coversheets attached to a shapeable member may be extensible, i.e., may exhibit some extensibility in response to tension forces applied in a cross sheet direction (where a cross sheet direction correspond generally to directions lying in a plane occupied by the coversheet when the coversheet is in a flat configuration) . A coversheet used in one or more embodiments of the shapeable articles described herein may be described as exhibiting tensile elongation (without tearing, ripping, etc.) of 10% or more, 20% or more, or 30% or more at a lower end in response to tensile forces applied in a cross sheet direction according to ASTM D5034 Grab tensile test. At an upper end, the coversheets used in one or more embodiments of the shapeable articles described herein may be described as exhibiting tensile elongation (up to failure (e.g., fracture, tearing, etc.)) of 1000% or less, 500% or less, 250% or less, 200% or less, 150% or less, 120% or less, or 110% or less according to ASTM D5034 Grab tensile test.

The extensibility of a coversheet used in one or more embodiments of shapeable articles as described herein may be elastic extensibility, where elongation of the coversheet may be substantially recovered after removal of any tensile forces causing the elongation. In one or more embodiments, one or both the coversheets on a shapeable article as described herein may recover 30% or more, 40% or more, or 50% or more of any elongation within 60 seconds or less of removal of any tensile forces causing elongation of a coversheet.

In one or more embodiments of the shapeable articles described herein, one or both of the coversheets 20 and 30 may include an outer surface 22 or 32, respectively, facing away from the shapeable member with a coefficient of friction that is, as described herein, high enough to assist in retention of tissues and/or organs, but also low enough such that excessive abrasion of tissues and organs does not occur during use of the shapeable articles in surgical procedures.

Such frictional properties are also, in one or more embodiments, found in shapeable articles that are fully hydrated with, e.g., water, normal saline (0.90% wt/wt sodium chloride in water), etc. In one or more embodiments, the outer surfaces of coversheets used in one or more embodiments of a shapeable member as described herein may exhibit a mean coefficient of friction of at least 0.2. At an upper limit, it may be beneficial to provide a shapeable article as described herein that includes an outer surface having a mean coefficient of friction of up to 0.45. In still other alternative embodiments, the outer surface of a shapeable article as described herein may exhibit a mean coefficient of friction of up to only 0.35.

The frictional properties of the outer surfaces of coversheets used in one or more embodiments of shapeable articles as described herein may be controlled using materials that are either used to construct the outer surface and/or coated on the outer surface. Some potentially suitable examples of materials and constructions that may provide desirable coefficients of friction are the materials containing silicone polyurea copolymers described in, e.g., U.S. Provisional Patent Application No. 62/417,146, filed Nov. 3, 2016, and titled SILICONE COPOLYMERS, METHODS OF MAKING, AND ARTICLES.

Figure 2:
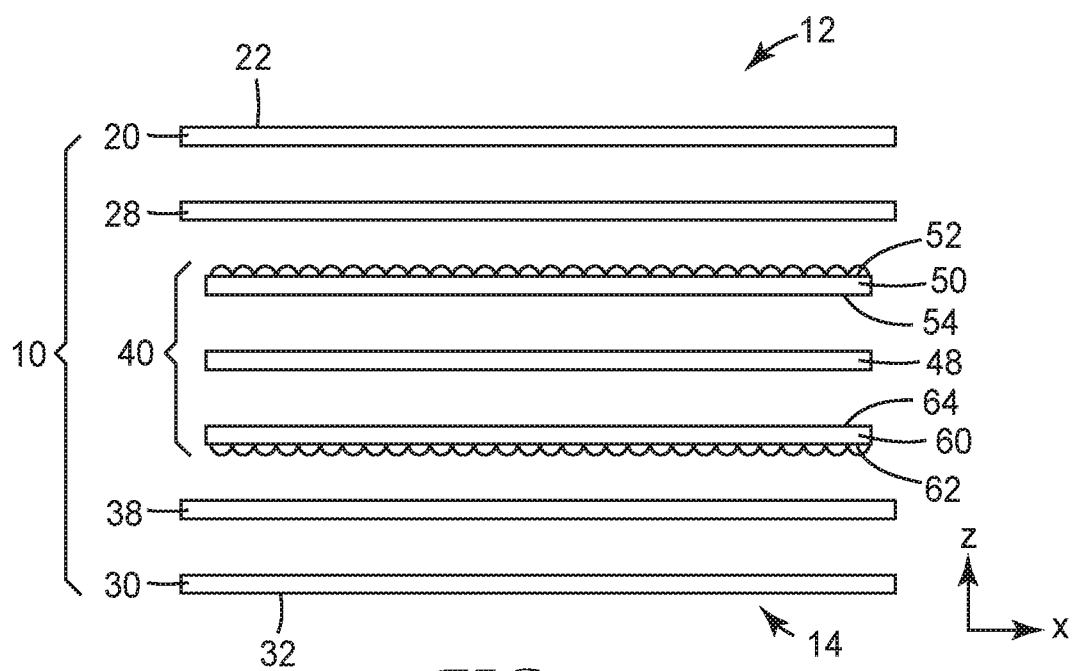
FIG. 2 is an exploded diagram depicting various components that may be found in one illustrative embodiment of a shapeable article as described herein.

One illustrative embodiment of components that may be found in a shapeable member 40 as provided in the shapeable article 10 is depicted in FIG. 2. The shapeable member 40 includes a first sheet 50 and a second sheet 60. Although the illustrative embodiment of shapeable article 10 includes a shapeable member 40 including two sheets 50 and 60 including structured elements as described herein, one or more alternative embodiments of shapeable articles as described herein may include only one sheet including structured elements as described herein.

In embodiments that include two sheets with structured elements, the first sheet 50 and second sheet 60 may be the same or different in one or more embodiments of shapeable articles as described herein. In one or more embodiments, such as that depicted in FIG. 2, the first sheet 50 may be attached to the second sheet 60 using adhesive 48. More specifically, the first sheet 50 includes a first major surface 52 facing away from the second sheet 60 and a second major surface 54 that faces towards the second sheet 60. Similarly, the second sheet 60 includes a first major surface 62 that faces away from the first sheet 50 and a second major surface 64 that faces towards the first sheet 50. The first and second major surfaces of both the first sheet 50 and the second sheet 60 are located on opposite sides of their respective sheets. Although adhesive 48 is depicted as a continuous layer located between the second major surfaces 54 and 64 of the first sheet 50 and the second sheet 60, the adhesive 48 may be provided as a continuous or discontinuous layer as discussed herein.

Figure 3:
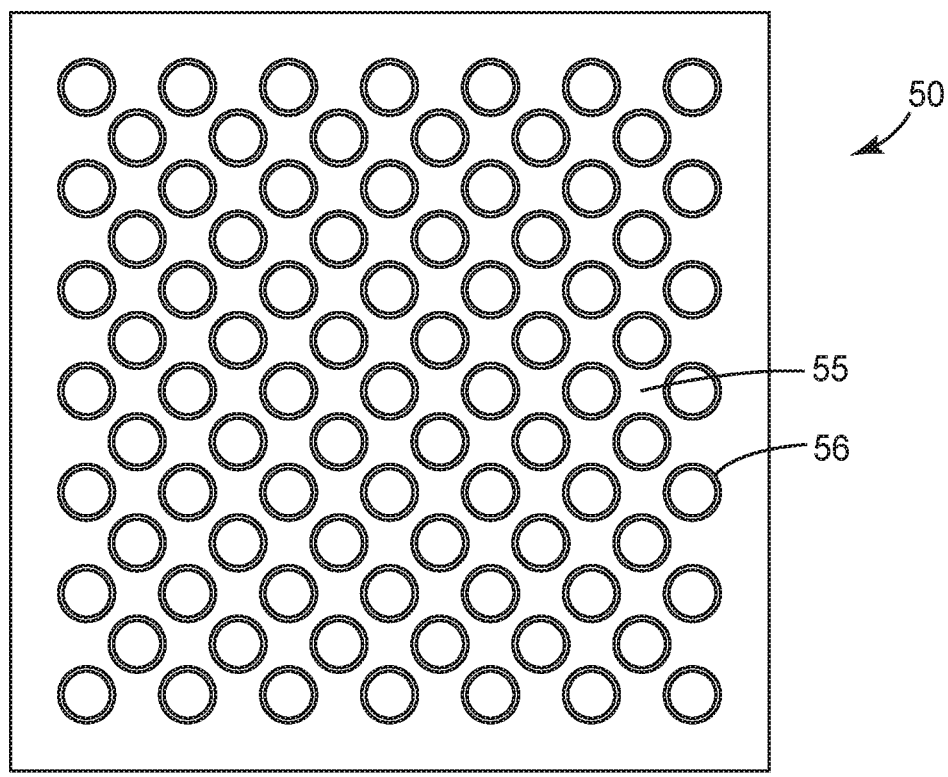
FIG. 3 depicts one illustrative embodiment of an arrangement of structured elements on a component that may be used in one or more illustrative embodiments of shapeable articles as described herein.

In one or more embodiments of the shapeable articles described herein, the first sheet 50 and/or the second sheet 60 may be described as having a land portion extending between and connecting a plurality of structured elements. FIG. 3 is a plan view of the first major surface of first sheet 50 of shapeable article 10. As seen in FIG. 3, first sheet 50 includes a land portion 55 extending between and connecting structured elements 56. As discussed above, second sheet 60 of shapeable article 10 may be the same or different from the first sheet 50.

Figure 4:
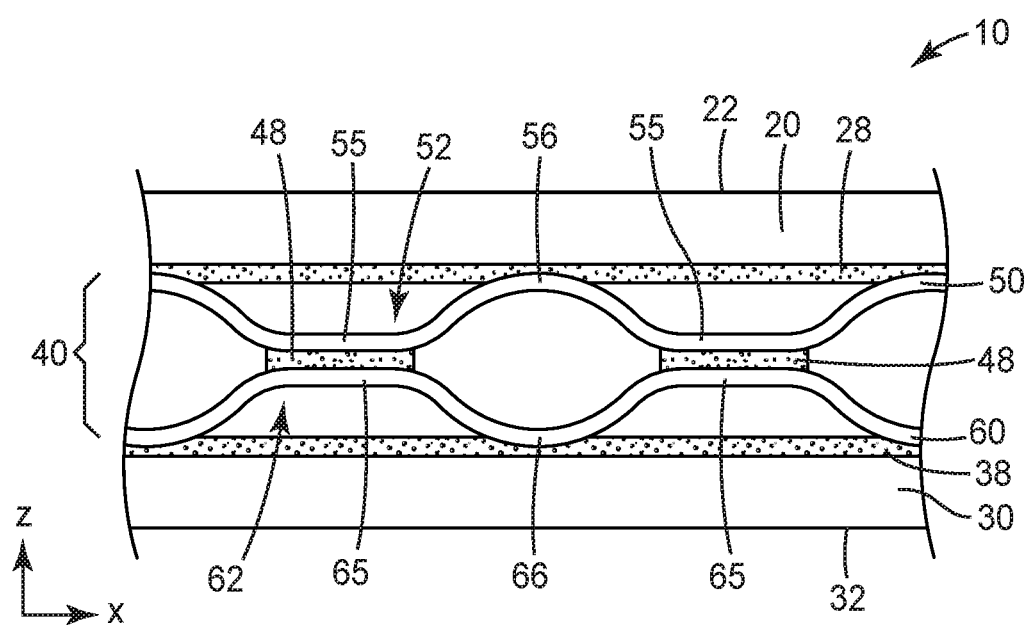
FIG. 4 is in an enlarged cross-sectional view of a portion of one illustrative embodiment of a shapeable article as described herein.

FIG. 4 is an enlarged cross-sectional view of a portion of shapeable article 10 after assembly of the components depicted in FIG. 2. As seen there, shapeable article 10 includes shapeable member 40 along with first coversheet 20 and second coversheet 30 attached thereto. First sheet 50 includes land portions 55 extending between and connecting structured elements 56. Although all of the structured elements 56 are separated by land portion 55 in the depicted embodiment, in one or more alternative embodiments, all of the structured elements 56 may not be separated by the land portion 55. Each of the structured elements 56 includes a depression on the second major surface 54 of the first sheet 50 (i.e., the surface of the first sheet 50 facing the second sheet 60). The depression formed by each of the structured elements 56 corresponds, in the depicted embodiment, to a protrusion extending from the first major surface 52 of the first sheet 56.

Similarly, second sheet 60 also includes land portion 65 extending between and connecting structured elements 66. Each of the structured elements 66 includes a depression on the second major surface 64 of the second sheet 60 (i.e., the surface of the second sheet 60 facing the first sheet 50). Although all of the structured elements 66 are separated by land portion 65 in the depicted embodiment, in one or more alternative embodiments, all of the structured elements 66 may not be separated by the land portion 65. The depression formed by each of the structured elements 66 corresponds, in the depicted embodiment, to a protrusion extending from the first major surface 62 of the first sheet 56.

In the embodiment depicted in FIG. 4, the structured elements 56 on the first sheet 50 are aligned with the structured elements 66 on the second sheet 60, where that alignment is along the Z axis as depicted in FIG. 4. In the depicted embodiment in which each structured element includes a depression and a corresponding protrusion, the depressions formed by the structured elements 56 and 66 face each other and may, in one or more embodiments, form a cell. Similarly, the land portion 55 between structured elements 56 on the first sheet 50 may also, in one or more embodiments, be aligned with the land portions 65 located between the structured elements 66 on the second sheet 60.

First sheet 50 is attached to second sheet 60 using adhesive 48 which, in the depicted embodiment, is limited to the land portion 55 of the first sheet 50 and the land portion 65 of the second sheet 60. In one or more alternative embodiments, adhesive connecting the first sheet 52 the second sheet 60 may extend over the entire facing surfaces of both the first sheet 50 and the second sheet 60 (i.e., the adhesive may not necessarily be limited to the land portions 55 and 65 of the first and second sheets 50 and 60). Furthermore, although adhesive 48 is shown on all of the land portion depicted in FIG. 4, in one or more alternative embodiments only some of the land portions of the first sheet 50 and second sheet 60 may include adhesive (e.g., the adhesive 48 may be pattern coated, etc.). The adhesive used to attach sheets 50 and 60 to each other may, in one or more embodiments, be a pressure sensitive adhesive such as, e.g., an acrylate, polyurethane, polyolefin, styrene copolymer or a combination thereof; a hot melt adhesive such as a polyolefin or modified polyolefin (ethylene vinylacetate, ethylene acrylates such as ethylene methylacrylate, acrylates such as KURARITY (from Kuraray) and the like), or a curable adhesive such a 2 part silicone, epoxy, or polyurethane. Additionally, in one or more alternative embodiments the first and second sheets 50 and 60 may be attached to each other using one or more other techniques such as, e.g., welding (one or more of thermal, chemical, and mechanical welding), sewing, mechanical fasteners (e.g., hook and loop fasteners, stem fasteners (e.g., 3M DUAL LOCK reclosable stem fasteners), etc.), riveting, stitching, crimping, etc. over any necessary portion of the sheets 50 and 60 to maintain the sheets in position relative to each other.

The cells formed by the structured elements 56 and 66 may, in one or more embodiments, provide structural advantages. In particular, the cells formed by structured elements 56 and 66 may result in bending of the shapeable member 40, when deformed from a flat, planar configuration such as that seen in, e.g., FIG. 1, that follows the land portions 55 and 65 connecting the structured elements 56 and 66. In other words, the cells formed by the structured elements 56 and 66 would not, themselves, typically bend in response to folding or manipulation of the shapeable article 10 and the shapeable member 40 located therein. Rather, bending preferably occurs in the land portions 55 and 65 between the structured elements 56 and 66.

The control over bending of the shapeable member 40 of one or more embodiments of shapeable articles as described herein may play a role in reducing pressure points that may be exerted on tissue/organs by the shapeable articles described herein. In particular, creases can be expected to form pressure points (i.e., local areas of increased pressure) when the shapeable articles described herein contact tissue/organs. As a result, reducing the likelihood and/or prominence of creases can play a role in reducing the likelihood of pressure points when using the shapeable articles described herein to restrain tissues/organs.

In the cross-sectional view of FIG. 4, the shapeable article 10 also includes a first coversheet 20 attached to the first major surface 52 of the first sheet 50 using, in the depicted embodiment, adhesive 28. Although adhesive 28 is shown as a continuous layer on first coversheet 20, it should be understood that in the adhesive used to attach the coversheet 20 to the first sheet 50 may be provided in a discontinuous pattern on the coversheet 20 and/or the first sheet 50. Further, in one or more alternative embodiments, the first coversheet 20 may be attached to first sheet 50 using one or more alternative techniques such as, e.g., welding, thermal and/or chemical, insert molding, compression molding, casting, flood coating, slot coating, spray coating, printing, thermal forming, thermal lamination, etc.

The shapeable article 10 depicted in FIG. 4 also includes a second coversheet 30 attached to the first major surface 62 of the second sheet 60 using, in the depicted embodiment, adhesive 38. Although adhesive 38 is shown as a continuous layer on second coversheet 30, it should be understood that any adhesive used to attach the coversheet 30 to the second sheet 60 may be provided in a discontinuous pattern on the coversheet 30 and/or second sheet 60.

In the embodiment depicted in FIG. 4, the first coversheet 20 is attached only to the protrusions formed by structured elements 56 and the second coversheet 30 is attached only to the protrusions formed by structured elements 66. In particular, the first coversheet 20 is not attached to the land portion 55 on the first major surface 52 of the first sheet 50. Similarly, the second coversheet 30 is not attached to the land portion 65 on the first major surface 62 of the second sheet 60. In one or more alternative embodiments, however, the first and second coversheet 20 and 30 may be attached over the entire major surfaces of their corresponding sheets 50 or 60. In still other embodiments, the coversheets 20 and 30 may be attached only to the land portions 55 and 65 of their respective sheets 50 and 60. In still other alternative embodiments, the first and/or second cover sheets may be attached to only some protrusions formed by the structured elements on their respective underlying sheets 50 or 60.

The shapeable article 10 as seen in, e.g., the enlarged cross-sectional view of FIG. 4 includes a shapeable member 40 constructed of a first sheet 50 and a second sheet 60 where each of the first and second sheets 50 and 60 include structured elements having protrusions 56 and 66 on their respective first major surfaces 52 and 62 along with corresponding depressions on their respective second major surfaces 54 and 64. As a result, the depressions form cavities in the shapeable member 40.

Although the depressions formed by opposing structured elements 56 and 66 and first and second sheets 50 and 60 are shown as facing each other in the embodiment depicted in FIG. 4, in one or more alternative embodiments the structured elements 56 and 66, when in the form of a protrusion and corresponding depression, may be provided in a nested arrangement. One example of a nested arrangement of structured elements 56 and 66 is depicted in the cross-sectional view of FIG. 5A. As seen in this illustrative embodiment, the protrusion formed by structured element 66 in second sheet 60 is located within the depression formed by structured element 56 in the first sheet 50. As a result, first major surface 62 of second sheet 60 faces in the same direction as the first major surface 52 of the first coversheet 50, while second major surface 64 of second coversheet 60 faces away from the first coversheet 50.

Figure 5A:
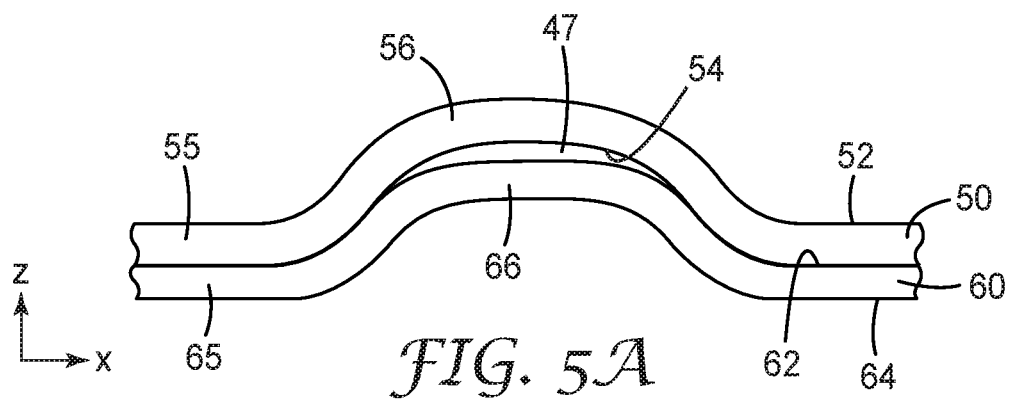
FIG. 5A is an enlarged cross-sectional view of an alternative illustrative embodiment of a portion of a shapeable article as described herein.

Another difference in the arrangement depicted in FIG. 5A versus that depicted in FIG. 4 is that the first and second coversheets 50 and 60 may be attached using adhesive 47 located between the protrusion formed by structured element 66 and the depression formed by structured element 56 rather than in the land portions 55 and 65 of the first and second coversheets 50 and 60. It should, however, be understood that adhesive could be provided in between the land portions 55 and 65 in addition to being located between the structured elements 56 and 66 or, in one or more alternative embodiments, adhesive may be located only between the land portions 55 and 65 in an arrangement such as that depicted in FIG. 5A.

Figure 5B:
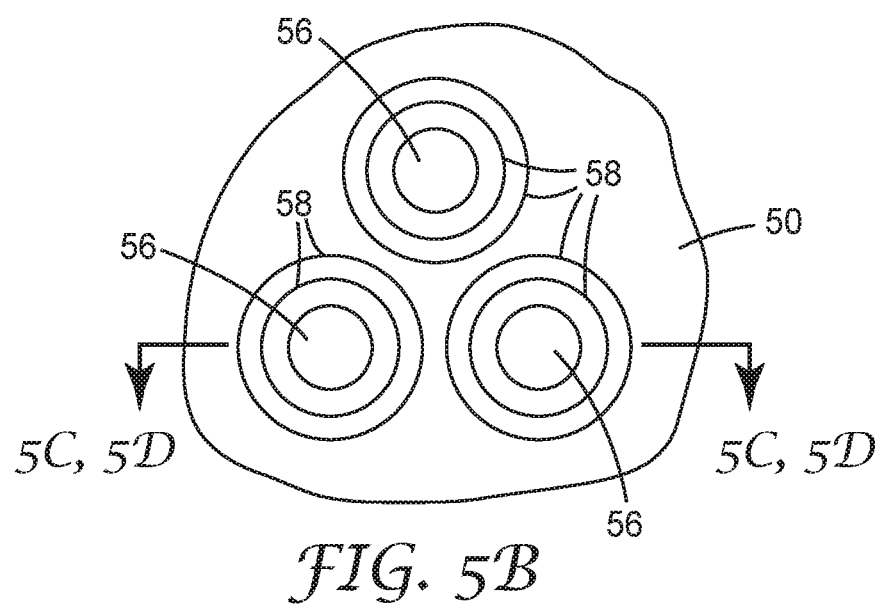
FIG. 5B is an enlarged plan view of a portion of another alternative illustrative embodiment of a shapeable article as described herein.
Figure 5C:
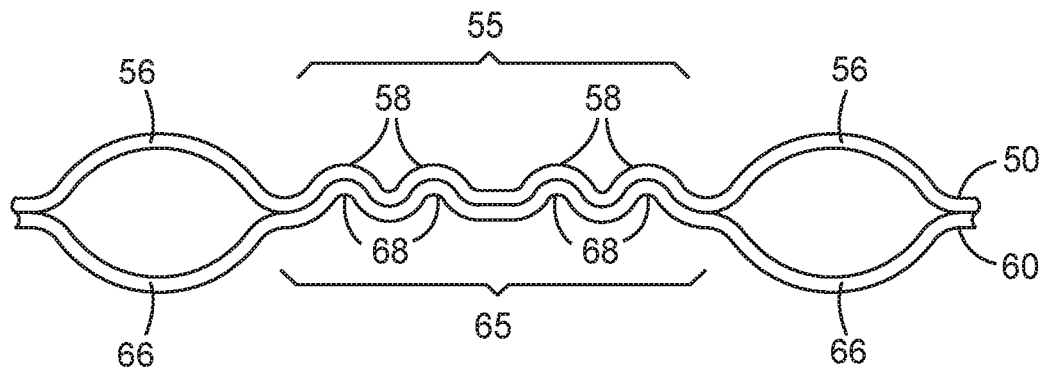
FIGS. 5C and 5D are cross-sectional views of two alternative illustrative embodiments of the shapeable article of FIG. 5B taken along line 5C/5D-5C/5D in FIG. 5B.
Figure 5D:
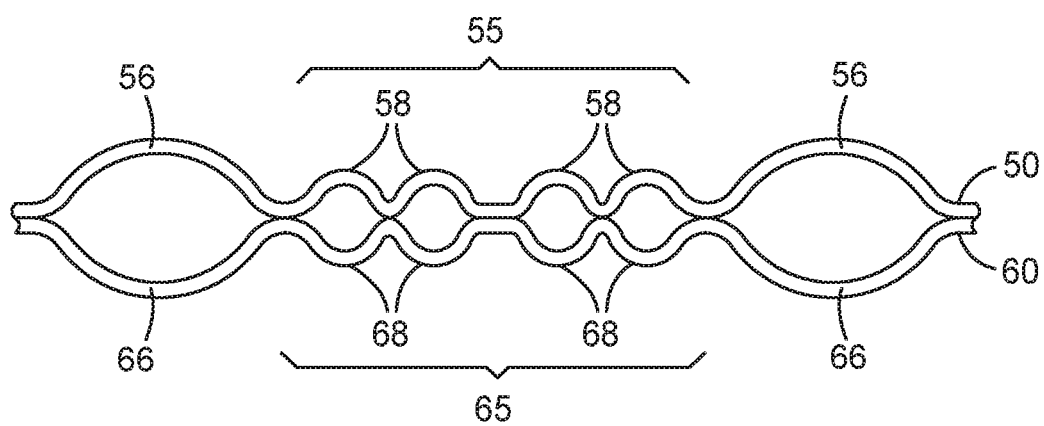

Another variation that may be found in one or more embodiments of shapeable articles as described herein is depicted in FIGS. 5B-5D. The variations depicted in those figures can be generally described as sheets that may be used to form a shapeable member 40 in which the land portions 55 located between structured elements 56 on a first sheet 50 and, correspondingly, land portions 65 located between structured elements 66 on a second sheet 60 are not flat as seen in, e.g., the illustrative embodiment depicted in the cross-sectional view of FIG. 4. Although not wishing to be bound by theory, the non-flat land portions may provide additional material between structured elements in a shapeable member 40 that may be beneficial for bending the shapeable member 40 in opposite directions, i.e., the shapeable member 40 including non-flat land portions may be more easily bent in a first direction and then later bent in a second direction that is opposite the first direction.

As seen in the plan view of FIG. 5B, one illustrative embodiment of a sheet 50 having non-flat land portions 55 may include a series of concentric rings 58 formed around one or more of the structured elements 56. In the cross-sectional view depicted in FIG. 5C, the first sheet 50 includes structured elements 56 having concentric rings 58 formed therein about each of the structured elements 56. In addition, the second sheet 60 includes structured elements 66 having concentric rings 68 formed therein about each of the structured elements 66.

In the illustrative embodiment depicted in the cross-sectional view of FIG. 5C, the concentric rings 58 in first sheet 50 and concentric rings 68 in second sheet 60 form a nested arrangement such that the concentric rings 68 in second sheet 60 extend into depressions formed in the surface of first sheet 50 that faces second sheet 60 by concentric rings 58. In embodiments including nested non-flat land portions such as the illustrative embodiment depicted in, e.g., FIG. 5C, the nested non-flat land portions may be useful in aligning/registering the sheets 50 and 60 such that the structured elements 56 and 66 are located in a selected arrangement relative to each other.

In one alternative, illustrative embodiment depicted in the cross-sectional view of FIG. 5D, the concentric rings 58 in first sheet 50 and concentric rings 68 in second sheet 62 not form the nested arrangement seen in FIG. 5C. Rather, the concentric rings 58 and 68 extend away from each other in a manner similar to the structured elements 56 and 66 on first and second sheets 50 and 60.

In either of the illustrative embodiments depicted in FIGS. 5C and 5D, additional material is available within the land portions 55 and 65 during deformation of the shapeable member 40 as described herein. Further, although not depicted in the cross-sectional views of 5C and 5D, the first and second sheet 60 may be attached to each other in the land portions by any suitable technique or combination of techniques as described elsewhere herein.

In addition, although concentric rings are located about all of the depicted structured elements, in one or more alternative embodiments, only some of the structured elements in any given sheet may include non-flat land portions (e.g., concentric rings). Further, although each of the structured elements includes two concentric rings, only one concentric ring or three or more concentric rings may be provided about any of the structured elements.

Further, although the structured elements 56 and 66 in FIGS. 5C and 5D are depicted in the same orientation as seen in, e.g., the cross-sectional view of FIG. 4, they could alternatively be nested as seen in, e.g., FIG. 5A.

Figure 5E:
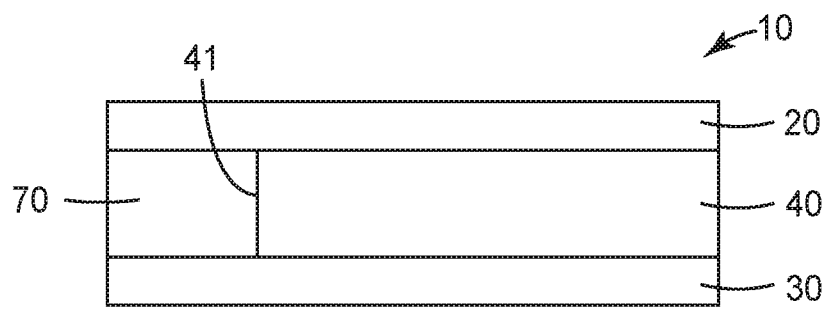
FIG. 5E is an enlarged cross-sectional view of an optional edge protector that may be incorporated into one or more embodiments of the shapeable articles as described herein.

Another optional feature that may be provided in one or more embodiments of shapeable articles as described herein is depicted and will be described in connection with FIG. 5E, which depicts an enlarged cross-sectional view of a portion of one illustrative embodiment of a shapeable article as described herein. As seen in FIG. 5E, the shapeable article 10 includes a shapeable member 40, a first coversheet 20, and a second coversheet 30. Both of the cover sheets 20 and 30 are attached to the shapeable member 40 as described elsewhere herein.

The additional optional feature depicted in FIG. 5E is an edge protector 70. In the depicted illustrative embodiment, the edge protector 70 is positioned proximate a perimeter 41 of the shapeable member 40. In one or more embodiments, at least a portion of the edge protector 70 is located between the first cover sheet 20 and the second cover sheet 30. Although the depicted illustrative embodiment of edge protector 70 depicts the edge protector 70 as having an exposed edge outside of the perimeter 41 of the shapeable member 40, in one or more alternative embodiments, one or both of the cover sheets 20 and/or 30 may extend past the edge protector 70 such that the edge protector 70 can be encased within one or both of the cover sheets 20 and/or 30 about the perimeter 41 of the shapeable member 40.

Further, it should be understood that edge protectors used in one or more embodiments of shapeable articles as described herein may take a variety of shapes. For example, although the edge protector 70 in the depicted illustrative embodiment has a generally rectangular shape, other embodiments of edge protectors may take any suitable shape. For example, in one or more embodiments, an edge protector used in one or more embodiments of a shapeable article as described herein may include a slot or channel capable of receiving an edge at the perimeter of a shapeable member as described herein.

In one or more embodiments, the edge protector 70 extends about at least a portion of the perimeter 41 of the shapeable member 40. In one or more embodiments, the edge protector 70 may extend about only a portion of the perimeter 41 of the shapeable member 40 which may be used in one or more embodiments of a shapeable article as described herein. For example, in one or more embodiments, the edge protector 70 may be located along only one side of a generally rectangular shapeable article 10. In one or more alternative embodiments, the edge protector 70 may extend around the entire perimeter 41 of a shapeable member 40 used in one or more embodiments of a shapeable article as described herein.

Edge protectors used in connection with one or more embodiments of a shapeable article as described herein may provide additional protection for tissue that contacts an edge of a shapeable article as described herein. In one or more embodiments, the edge protectors used in connection with one or more embodiments of a shapeable article as described herein may be formed of one or more compressible materials such as, e.g., those described herein with respect to cover sheets used in shapeable articles as described herein.

Edge protectors used in connection with one or more embodiments of shapeable articles as described herein may be attached to one or both of the cover sheets and/or the shapeable member used in the shapeable article by any suitable technique or combination of techniques. For example, in one or more embodiments, one or more adhesives may be used to attach the edge protectors to cover sheets and/or a shapeable member of a shapeable article. Potentially useful adhesives may, in one or more embodiments, include a pressure sensitive adhesive such as, e.g., an acrylate, polyurethane, polyolefin, styrene copolymer or a combination thereof; a hot melt adhesive such as a polyolefin or modified polyolefin (ethylene vinylacetate, ethylene acrylates such as ethylene methylacrylate, acrylates such as KURARITY (from Kuraray) and the like), or a curable adhesive such a 2 part silicone, epoxy, or polyurethane. Alternatively, or in addition to adhesives, the edge protectors used in one or more embodiments of shapeable articles as described herein may be attached to one or both of the cover sheets and/or the shapeable member using one or more other techniques such as, e.g., welding (one or more of thermal, chemical, and mechanical welding), sewing, mechanical fasteners (e.g., hook and loop fasteners, stem fasteners (e.g., 3M DUAL LOCK reclosable stem fasteners), etc.), riveting, stitching, crimping, etc.

Figure 6:
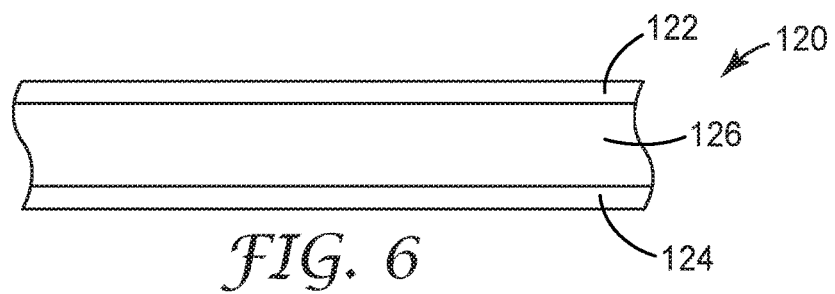
FIG. 6 is an enlarged cross-sectional view of a portion of another illustrative embodiment of a multilayer coversheet that may be used in one or more embodiments of the shapeable articles described herein.

Although the cover sheets on shapeable member 40 as depicted in, e.g., FIG. 4 include a single layer of material, coversheets used in connection with shapeable members to form shapeable articles as described herein may be constructed of two or more layers of materials. One illustrative embodiment of a coversheet 120 including multiple layers is depicted in FIG. 6. In that depicted illustrative embodiment, coversheet 120 includes a base layer 124, an intermediate layer 126 and an outer covering 122. Although the depicted illustrative embodiment of coversheet 120 includes three layers, it should be understood that coversheet used on shapeable articles as described herein may include only two layers or more than three layers.

The various components of the coversheet 120 may, in one or more embodiments, include one or more layers selected from a foam layer, a polymeric film, a nonwoven sheet, a woven sheet, a knitted sheet, a mesh sheet, a net sheet, etc. as described herein with respect to other illustrative embodiments of coversheets used in shapeable articles as described herein. Any compressible (e.g., foam, etc.) layers provided in coversheet 120 may include characteristics described herein with respect to other compressible (e.g., foam, etc.) layers in other coversheets used in other illustrative embodiments of shapeable articles as described herein.

In one or more embodiments, the base layer 124 may be formed of an extensible material which, in some instances, may be an elastically extensible material. In one or more embodiments of shapeable articles as described herein, the base layer 124 may exhibit a tensile elongation in the ranges described herein.

The intermediate layer 126 may provide, in one or more embodiments, properties such as pressure distribution (where, for example, the intermediate layer is a compressible layer such as, e.g., a foam layer, gel, lofted woven or nonwoven, etc.). In one or more embodiments, the intermediate layer 126 may also be a hydrophilic layer capable of absorbing and carrying liquids such as, e.g., water and/or normal saline.

The outer covering 122 may be provided to protect the intermediate layer 126 of the coversheet 120. The outer covering 122 may, in one or more embodiments, also provide a coefficient of friction to the outer surface of the coversheet 120 that is within the selected ranges as discussed herein to limit abrasion on tissues and/or organs while retaining sufficient frictional properties to function as needed in restraining tissues and/or organs as discussed herein.

Although the outer covering 122, base layer 124 and intermediate layer 126 are described as having certain characteristics, it should be understood that any of the layers may have any of the described characteristics. For example, although the intermediate layer 126 is described as providing pressure distribution and/or being hydrophilic, one or both of the outer covering 122 and/or base layer 124 may possess these characteristics in place of or in addition to intermediate layer 126.

Figure 7:
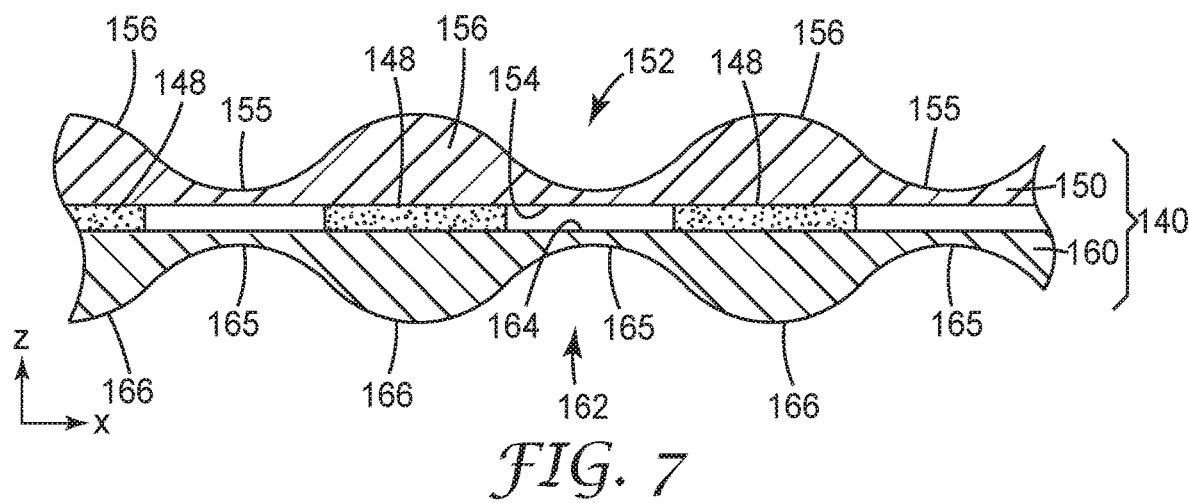
FIG. 7 is an enlarged cross-sectional view of a portion of another illustrative embodiment of a shapeable member that may be used in one or more embodiments of the shapeable articles described herein.

Another alternative illustrative embodiment of a shapeable member 140 is depicted in FIG. 7 in which the protrusions formed by structured elements on the first and second sheets do not include corresponding depressions but are, instead solid features formed in the first and second sheets. In particular, shapeable member 140 includes a first sheet 150 and a second sheet 160. First sheet 150 includes a first major surface 152 facing away from the second sheet 160 while second sheet 160 includes a first major surface 162 that faces away from the first sheet 150. First sheet 150 also includes a second major surface 154 that faces the second sheet 160, while second sheet 160 includes a second major surface 164 that faces the first sheet 150. Unlike embodiments in which the protrusions formed by structured elements have a corresponding depression, the structured elements in first and second sheets 150 and 160 are in the form of solid features that extend from the second major surface 154 or 164 to the first major surface 152 or 162 for each of the first and second sheets 150 and 160.

First sheet 150 includes land portions 155 extending between and connecting structured elements 156. Each of the structured elements 156 on the first sheet 150 forms a protrusion extending from the first major surface 152 of the first sheet 150. Similarly, second sheet 160 includes land portions 165 extending between and connecting structured elements 166, where each of the structured elements 166 on the second sheet 160 forms a protrusion extending from the first major surface 162 of the second sheet 160. In the embodiment depicted in FIG. 6, the structured elements 156 on the first sheet 150 are aligned with the structured elements 166 on the second sheet 160, where that alignment is along the Z axis as depicted in FIG. 7, although such an arrangement may not be required.

First sheet 150 is, in the illustrative embodiment depicted in FIG. 7, attached to second sheet 160 using adhesive 148 which, in the depicted embodiment, is positioned between the protrusions formed by the structured elements 156 and is not provided between the land portion 155 of the first sheet 150 and the land portion 165 of the second sheet 160. In one or more alternative embodiments, adhesive connecting the first sheet 150 to the second sheet 160 may be located between the land portions of the first and second sheets 150 and 160 but not between the structured elements 156 and 166. In another alternative embodiment, adhesive may extend over the entire facing surfaces of both the first sheet 150 and the second sheet 160. Additionally, in one or more alternative embodiments the first and second sheets 150 and 160 may be attached to each other using one or more other techniques such as, e.g., welding (one or more of thermal, chemical, and mechanical welding), sewing, mechanical fasteners (e.g., hook and loop fasteners, stem fasteners (e.g., 3M DUAL LOCK reclosable stem fasteners), etc.), riveting, stitching, crimping, etc. over any necessary portion of the sheets 150 and 160 to maintain the sheets in position relative to each other.

The structured elements 156 and 166 may, in one or more embodiments, be described as cells that may provide structural advantages. In particular, the cells formed by structured elements 156 and 166 may result in bending of the shapeable member 140 (when deformed from a flat, planar configuration such as that seen in, e.g., FIG. 1) that follows the land portions 155 and 165 connecting the structured elements 156 and 166. In other words, the cells formed by structured elements 156 and 166 would not, themselves, typically bend in response to folding or manipulation of a shapeable article containing shapeable member 140. Rather, bending preferably occurs in the land portions 155 and 165 between the structured elements 156 and 166.

The sheets used in shapeable members as described herein may be constructed of a variety of different materials. For example, sheets including structured elements in the shapeable members may, in one or more embodiments, be constructed of a malleable/ductile metal such as, e.g., aluminum, copper, stainless steel, etc. The sheets may be, for example, constructed of a malleable/ductile metal foil. In one or more embodiments, the sheets including structured elements may consist essentially of a metal foil. Suitable metal foils may include, e.g., continuous sheets of 1100 Series aluminum foils with a thickness of, e.g., 0.005 inches (about 0.127 millimeters).

In other alternative embodiments, the sheets including structured elements or other components used to manufacture shapeable members as described herein may include a layer of a metal foil along with one or more other layers. In one or more embodiments, for example, a metal foil may be embossed or otherwise manipulated to form the structured elements as described herein. In embodiments such as, e.g., the shapeable member depicted in FIG. 7, sheets may be constructed of malleable metals that are not in the form of a foil having a uniform thickness (e.g., the construction seen in FIG. 7 may be manufactured through stamping, casting, electroplating, etc.).

The malleable metal provided in sheets including structured elements as described herein may be used to provide malleability to the sheet and, therefore, the shapeable member. In particular, malleability, as used herein, is used to describe that the sheet is configured to be plastically deformed in response to manipulation forces and can hold a selected shape after the forces used to plastically deform the sheet are removed.

Although metal foil layers may be particularly useful to provide malleability to a sheet including structured elements in a shapeable member as described herein, in still other alternative embodiments, the sheet including structured elements may be constructed of materials that do not include a metal foil to provide malleability. For example, shape memory polymers, metal/polymeric composites, highly filled polymeric compositions generally having greater than 50%, 60%, and even 70% wt/wt filler (e.g., one or more inorganic fillers, etc.), etc.

Figure 8:
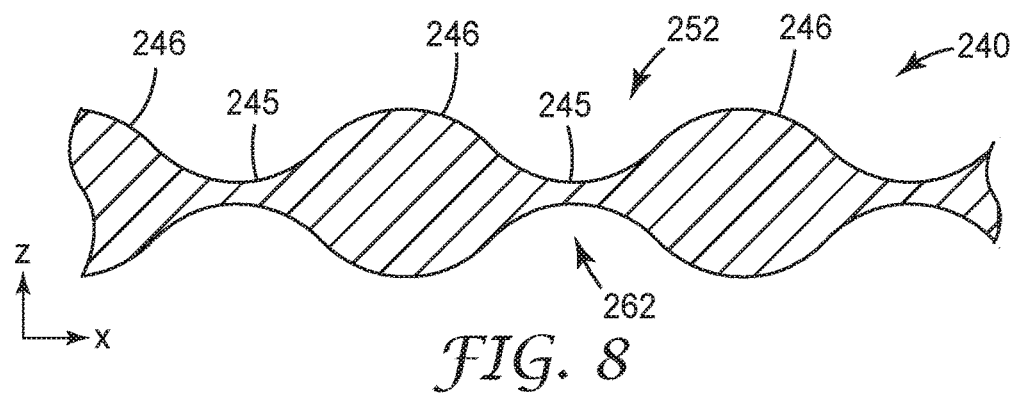
FIG. 8 is an enlarged cross-sectional view of a portion of another illustrative embodiment of a unitary shapeable member that may be used in one or more embodiments of the shapeable articles described herein.

Another alternative illustrative embodiment of a shapeable member 240 is depicted in FIG. 8 in which the shapeable member 240 includes structured elements 246 in a unitary shapeable member 240, i.e., a shapeable member that does not include two or more sheets providing the protrusions of structured elements as described in other illustrative embodiments herein. In particular, shapeable member 240 includes a first major surface 252 and a second major surface 262, with land portions 245 extending between and connecting structured elements 246 that form protrusions on both the first and second major surfaces 252 and 262 of the shapeable member 240.

In the embodiment depicted in FIG. 8, the structured elements 246 form protrusions on the opposite major surfaces 252 and 262 that are aligned along the Z axis as depicted in FIG. 8. Such an arrangement may, however, not be required.

Unitary shapeable members such as, e.g., shapeable member 240, may be constructed of a variety of different materials. For example, the unitary shapeable members may, in one or more embodiments, be constructed of a malleable metal such as, e.g., aluminum, copper, stainless steel, etc. In one or more embodiments, the unitary shapeable members described herein may consist essentially of one or more malleable metals. In one or more embodiments, unitary shapeable members as described herein may be manufactured through stamping, casting, electroplating, physical vapor deposition, sputtering, etc.

The malleable metal provided in unitary shapeable members as described herein may be used to provide malleability to the shapeable member. In particular, malleability, as used herein, is used to describe that the shapeable member is configured to be plastically deformed in response to manipulation forces and can hold a selected shape after the forces used to plastically deform the shapeable member are removed. In one or more embodiments, this is accomplished by incorporating a ductile metal sheet which may be continuous, perforated, or porous.

Although malleable metals may be particularly useful to provide malleability to a unitary shapeable member as described herein, in still other alternative embodiments, the unitary shapeable member may be constructed of any material or materials that provide malleability, e.g., shape memory polymers, metal/polymeric composites, highly filled polymeric compositions generally having greater than 50, 60, and even 70% wt/wt filler (e.g., one or more inorganic fillers, etc.), etc.

Figure 9:
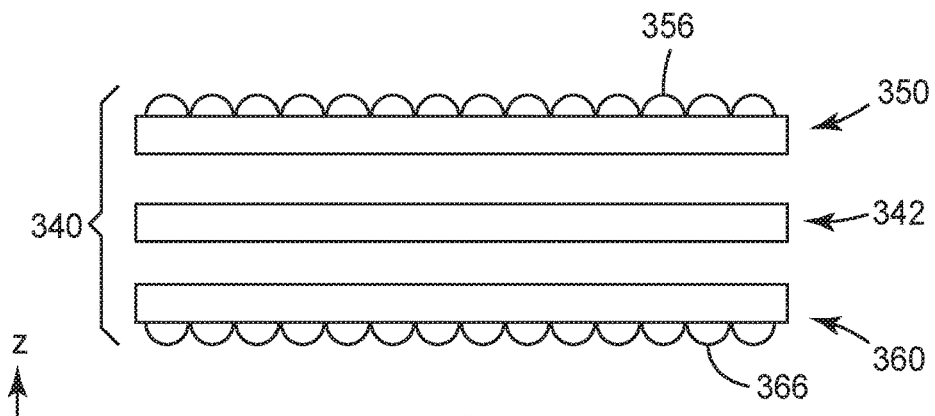
FIG. 9 is an exploded diagram depicting various components that may be found in another illustrative embodiment of a shapeable member that may be used in one or more embodiments of the shapeable articles described herein.

Although malleable metal sheets including structured elements as described herein may be used to provide malleability to shapeable articles as described herein, in one or more alternative embodiments, a malleable core may be provided in a shapeable member to provide malleability to the shapeable member that is not provided by sheets including structured elements. One illustrative embodiment of such an arrangement is depicted in FIG. 9 in which a first sheet 350 including structured elements 356 and a second sheet 360 including structured elements 366 are provided with a malleable core 342 located between the sheets 350 and 360. The sheets 350 and 360, when attached to malleable core 342, form a shapeable member 340 that can be used in a shapeable article as described herein.

The malleable core 342 in a construction such as that depicted in FIG. 8 may consist essentially of a metal foil in one or more embodiments, but in other alternative embodiments, the malleable core 342 may include one or more layers of metal foil, strips of metal foil, metal mesh, metal screens, perforated metal sheets, porous metal sheets (formed from, e.g., sintered metallic particles or metal nonwovens formed from metallic fibers, etc.), etc. to provide malleability to the shapeable member 340. In still other embodiments, the malleable core 342 may be constructed of materials that do not include a metal foil to provide malleability. For example, shape memory polymers, metal/polymeric composites, highly filled polymeric compositions generally having greater than 50, 60, and even 70% wt/wt filler (e.g., one or more inorganic fillers, etc.), etc.

In embodiments in which a malleable core 342 is provided, one or both of the sheets including structured elements located thereon may be provided of a variety of materials. For example, in one or more embodiments, one or both of the sheets 350 and 360 may be provided in the form of a polymeric sheet including both land portions and structured elements 356 or 366 as described herein. In one or more alternative embodiments, one or both of the sheets 350 and 360 may consist essentially of a polymeric sheet that forms both the land portions and the structured elements of a given sheet used in a shapeable member of shapeable article as described herein.

The structured elements and land portions used in shapeable members of shapeable articles as described herein may take a variety of different shapes and/or arrangements. For example, as seen in FIG. 3, all of the structured elements 56 on the first sheet 50 have the same shape as well as the same size. In one or more alternative embodiments, however, the structured elements 56 on the first sheet may have different shapes and/or different sizes. Furthermore, in one or more embodiments, the structured elements 66 on the second sheet 60 may also be provided with the same shape as well as the same size, although in one or more alternative embodiments the structured elements 66 on the second sheet may have different shapes and/or different sizes.

As also seen in the illustrative embodiment depicted in FIG. 3, the structured elements 56 on the first sheet 50 are arranged in a uniformly spaced array on the first sheet 50. Similarly, the structured elements 66 on the second sheet 60 may also be arranged in a uniformly spaced array on the second sheet 60. In one or more alternative embodiments, however, the structured elements on sheets used in shapeable members of shapeable articles as described herein may or may not be arranged in a uniformly spaced array.

Another manner in which the land portions and structured elements on sheets used in the shapeable members of shapeable articles as described herein may be characterized is in the portion of the surface area occupied by the land portions and/or the structured elements (regardless of whether or not the structured elements have the same size or shape or are or are not arranged in a uniformly spaced array). In one or more embodiments of the shapeable articles described herein, the land portion occupies 15% or more of a projection of the first major surface of the first sheet when the first major surface is flat and projected onto a plane. At an upper end, one or more embodiments of the shapeable articles described herein may include a land portion that occupies 70% or less of a projection of the first major surface of the first sheet when the first major surface is flat and projected onto a plane (where the plane is defined by the X and Y axes).

In terms of area occupied by the structured elements, in one or more embodiments of the shapeable articles described herein, the structured elements occupy 15% or more of a projection of the first major surface of the first sheet when the first major surface is flat and projected onto a plane. At an upper end, one or more embodiments of the shapeable articles described herein may include structured elements that occupy 70% or less of a projection of the first major surface of the first sheet when the first major surface is flat and projected onto a plane.

Figure 10:
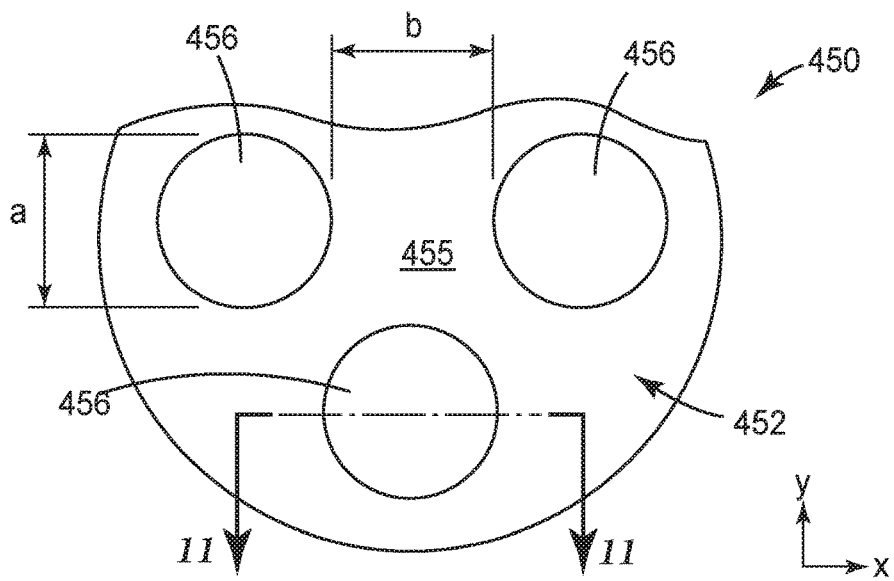
FIG. 10 is an enlarged view of a portion of one illustrative embodiment of a shapeable article as described herein depicting one illustrative arrangement of structured elements as described herein.

An enlarged view of a portion of the first major surface 452 of another illustrative embodiment of a sheet 450 that may be used in one or more embodiments of a shapeable article as described herein is depicted in FIG. 10. In one or more embodiments of shapeable articles as described herein, each of the structured elements 456 on the sheet 450 may be characterized in terms of the size of the structured elements 456. For example, in one or more embodiments of the shapeable articles as described herein, the structured elements 456 on the sheet 450 may have a maximum cross-sheet dimension (a) of 2.5 centimeters or less when the land portion 455 of the second major surface 454 of the sheet 450 is in a flat configuration (in one illustrative embodiment, the maximum cross-sheet dimension (a) may be, e.g., 1 centimeter or less). The structured elements on another sheet paired with the sheet 450 may also, in one or more embodiments, have the same dimensions as structured elements 456 on the sheet 450 although, in one or more alternative embodiments, the structured elements on the other sheet may have different dimensions.

Also with reference to FIG. 10, one or more embodiments of the shapeable articles as described herein may be characterized in terms of the distance between the structured elements 456. For example, in one or more embodiments of the shapeable articles as described herein, the structured elements 456 of two or more neighboring structured element pairs on the sheet 450 may be separated from each other by the land portion 455 by a maximum inter-element distance (b) of 2.5 centimeters or less when the land portion 455 of the second major surface 454 is in a flat configuration (in one or more embodiments, the maximum cross-sheet dimension (b) may be, e.g., 0.5 centimeter or less). Neighboring structured element pairs of structured elements on another sheet attached the sheet 450 depicted in FIG. 10 may also, in one or more embodiments, have the same inter-element distances as structured elements 456 although, in one or more alternative embodiments, the structured elements on the other sheet may have different inter-element distances.

In one or more embodiments, the maximum cross-sheet dimension (a) of the structured elements on a sheet may be equal to or greater than maximum inter-element distance (b).

In one or more embodiments of the shapeable articles as described herein, the structured elements may be described in terms of their height. With reference to the cross-sectional view depicted in FIG. 11, the protrusions of the structured elements 456 may have a height (h) measured from the land portion 455 on the second major surface 454 surrounding the structured element 456 when the land portion 455 of the second major surface 454 is in a flat configuration. In one or more embodiments of the shapeable articles described herein, the height (h) of the structured elements 456 may be 2 centimeters or less, or even 1 centimeter or less (where the height is also greater than zero).

Figure 11:
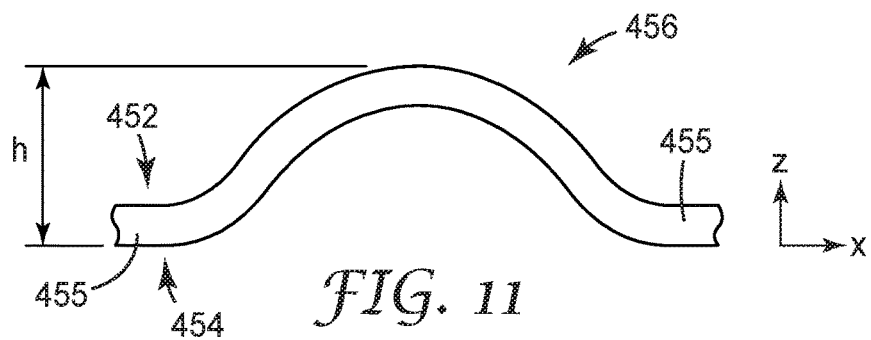
FIG. 11 is an enlarged cross-sectional view of a portion of one structured element taken along line 11-11 in FIG. 10.

Although the illustrative embodiments of structured elements 56 and 66 in FIGS. 4 and 456 in FIG. 11 are depicted as being unfilled, the structural elements in sheets used in shapeable members of one or more embodiments of shapeable articles as described herein may be filled to further affect the malleability and other properties of the shapeable articles. The structured elements may, in one or more embodiments, be filled with various materials including, e.g., polymers, filled polymers, foams such as polyurethane foams, and the like. Both thermoplastic and thermoset polymers may be used. Suitable thermoplastic polymers may include polyolefins, such as metallocene polyethylenes such as ENGAGE polyethylenes (commercially available from Dow Chemical Company, Midland Mich.), LDPE, LLDPE, polypropylene, polyurethanes such as polyester or polyether polyurethanes (e.g., ESTANE thermoplastic polyurethane commercially available from B. F. Goodrich, Cleveland Ohio), polyesters such as polyether polyester (e.g., HYTREL polyester elastomer commercially available from Du Pont Co., Wilmington, Del.), and polyamides such as polyether polyamides (e.g., PEBAX resins commercially available from ELF Atochem, North America, Inc., Philadelphia, Pa.) and acrylic block copolymers such as KURARITY block polyacrylates available from Kuraray America, Houston Tex. Low Tg thermoplastic polymers having a Tg less than room temperature may also be suitable and include adhesives such as, e.g., acrylics, polyurethanes and the like. Thermosets also may be suitable such as, e.g., two part silicones, epoxies, polyurethanes and polyureas. Light or heat curable thermosets also may be used such as, e.g., free radical cured polymers such as acrylates unsaturated polyesters or other unsaturated curable material.

Figure 12:
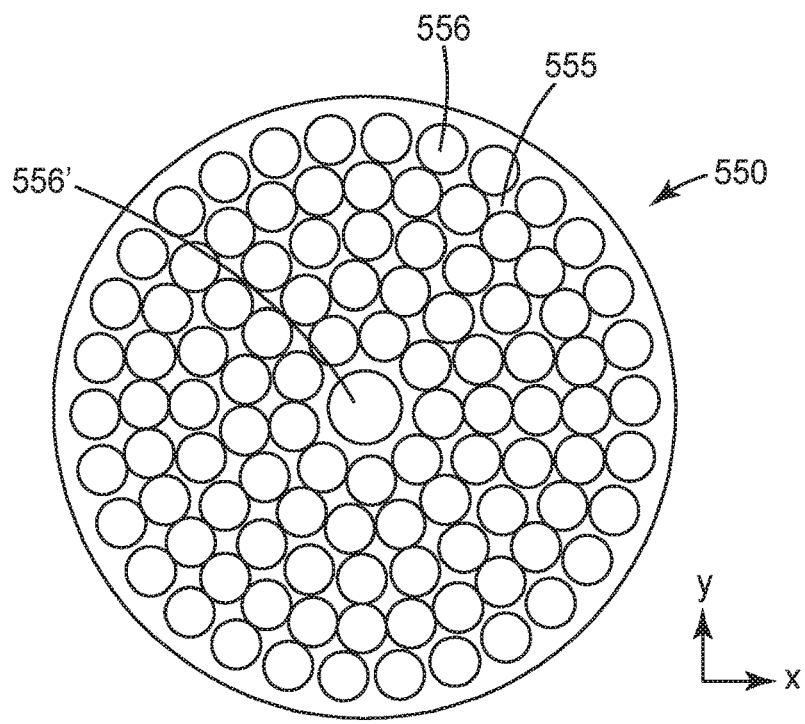
FIG. 12 depicts another illustrative embodiment of an arrangement of structured elements on a component that may be used in one or more illustrative embodiments of shapeable articles as described herein.

Although the structured elements on sheets in shapeable members as described herein may be provided in a uniform rectilinear array (see, e.g., first sheet 50 as depicted in FIG. 3), in one or more alternative embodiments of shapeable articles as described herein one or both of the sheets provided in the shapeable member may include structured elements arranged in any pattern or in no pattern. For example, one potential alternative embodiment of a sheet 550 including structured elements 556 separated from each other by a land portion 555 is depicted in FIG. 12. This depicted embodiment includes structured elements 556 arranged in a generally circular pattern around a central structured element 556'. Another variation in this depicted alternative embodiment is that the central structured element 556' is larger than the surrounding structured elements 556, illustrating one alternative in which all of the structured elements on a sheet used in a shapeable member of a shapeable article as described herein may not all have the same size.

Figure 13:
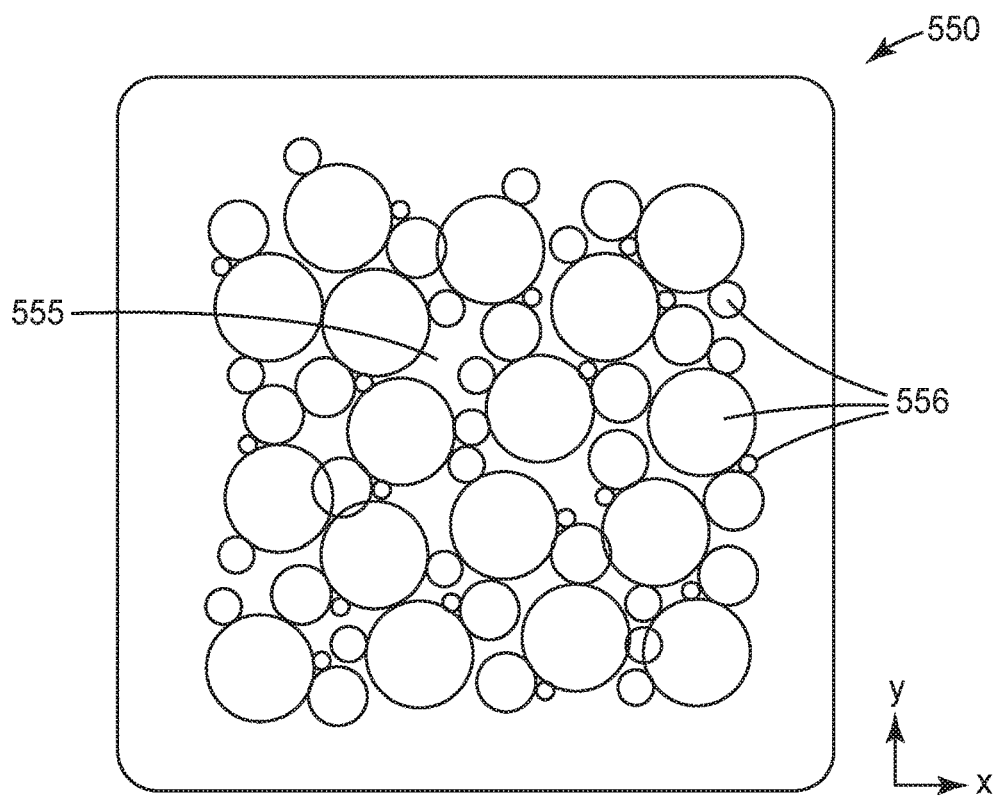
FIG. 13 depicts another illustrative embodiment of an arrangement of structured elements on a component that may be used in one or more illustrative embodiments of shapeable articles as described herein.

Although the structured elements of shapeable members described herein may be in generally ordered arrays (e.g., rectilinear, circular, etc.), FIG. 13 depicts another alternative embodiment in which a set of structured elements 556 on a sheet 550 separated by land portion 555 may include structured elements 556 having different sizes and arranged in a non-repeating, non-uniform manner. In one or more embodiments, the arrangement of structured elements 556 on sheet 550 as depicted in FIG. 13 may be described as a random arrangement.

In one or more embodiments in which the structured elements of a shapeable member have a generally circular shape when viewed in a plan view of a major surface of the shapeable member, the structured element may be described as having a spherical dome-shaped protrusion. Structured elements that have a generally circular shape may, however, have a protrusion that is not a spherical dome-shaped structure. For example, the protrusion may, in one or more alternative embodiments, be flattened or otherwise deviate from a spherical dome shaped structure.

In still other embodiments, the structured elements on a sheet used in a shapeable member of a shapeable article as described herein may be provided in shapes other than circular. For example, one illustrative embodiment of a shapeable member 540 including structured elements 556 having hexagonal shapes and being separated by a land portion 555 is depicted in FIG. 14.

Figure 15:
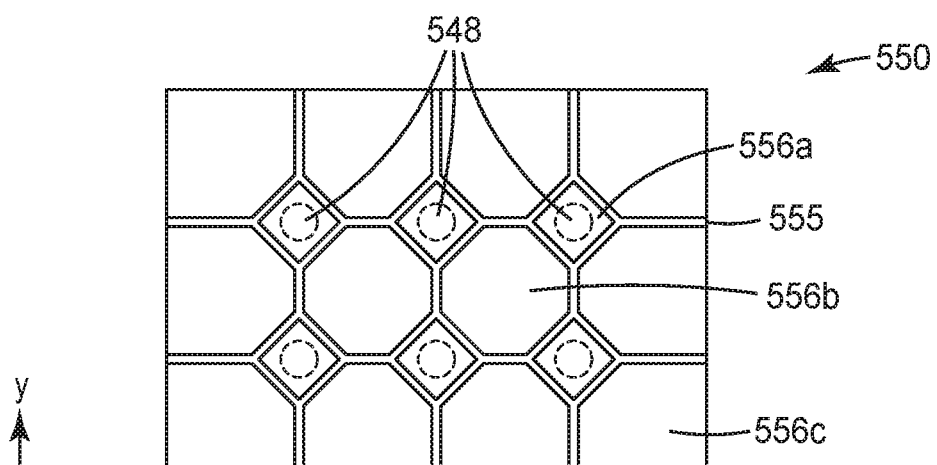

Another illustrative embodiment of a shapeable member 540 is depicted in FIG. 15 and includes structured elements having different shapes. In particular, shapeable member 540 as depicted in FIG. 15 includes rectangular (square) structured elements 356a as well as octagonal structured elements 356b, all of which are separated by land portion 355.

Figure 16:
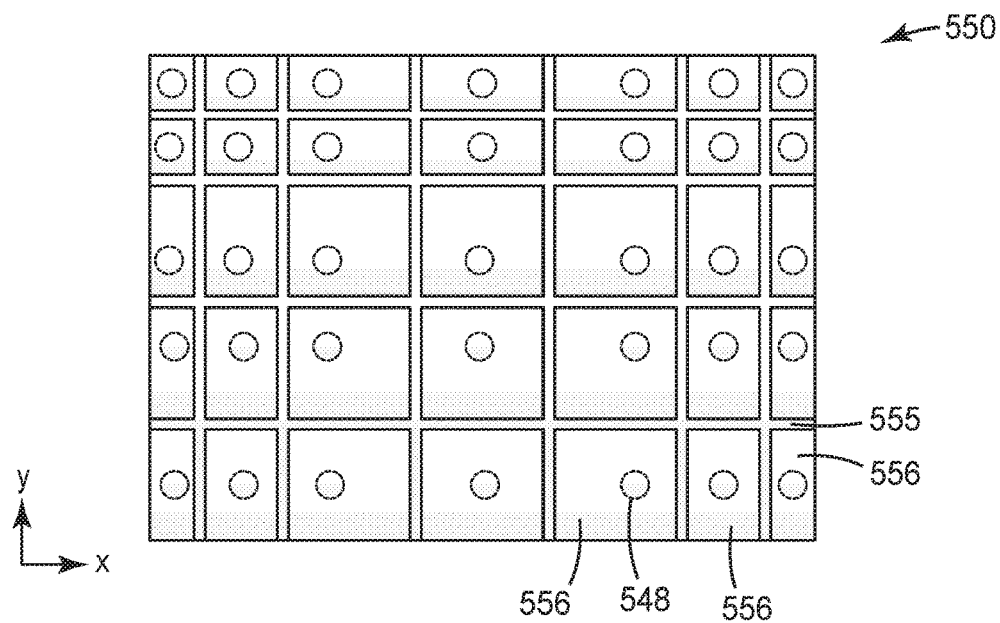

Yet another illustrative embodiment of a shapeable member 540 is depicted in FIG. 16 and includes structured elements 556 in different rectangular shapes, all of which are separated by land portion 555. In particular it may be beneficial to provide smaller or larger structured elements 556 in various locations and/or groupings on a shapeable member 540 to adjust the flexibility of the shapeable member 540.

Figure 14:
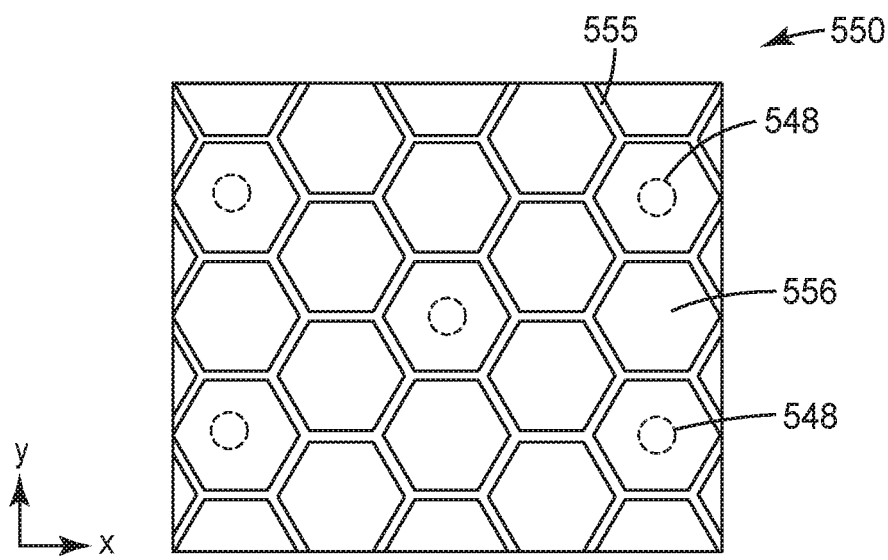
FIGS. 14-16 depict alternative embodiments of structured elements of varying sizes, shapes, and arrangements which may be used in one or more embodiments of shapeable members used in shapeable articles as described herein.

Another optional feature of one or more embodiments of shapeable articles as described herein can also be described in connection with the various illustrative embodiments of shapeable members 540 as depicted in FIGS. 14-16. Each of the shapeable members 540 includes selected areas 548 where a coversheet may be attached to the structured elements of each of the shapeable members 540. In particular, the illustrative embodiments depicted in FIGS. 14 and 15 demonstrate one variation in which only some of the structured elements are attached to a coversheet extending over the surface containing those structured elements. Limiting the points of attachment between a coversheet and an underlying set of structured elements may, in one or more embodiments, improve flexibility of the shapeable article so constructed.

The illustrative embodiment of shapeable member 540 as depicted in FIG. 16, however, demonstrates another variation in which all of the structured elements 556 are attached to a coversheet extending over the surface containing those structured elements. Increasing the number of points of attachment between a coversheet and an underlying set of structured elements may, in one or more embodiments, provide a more robust construction, limit flexibility in a positive manner, etc.

Figure 17:
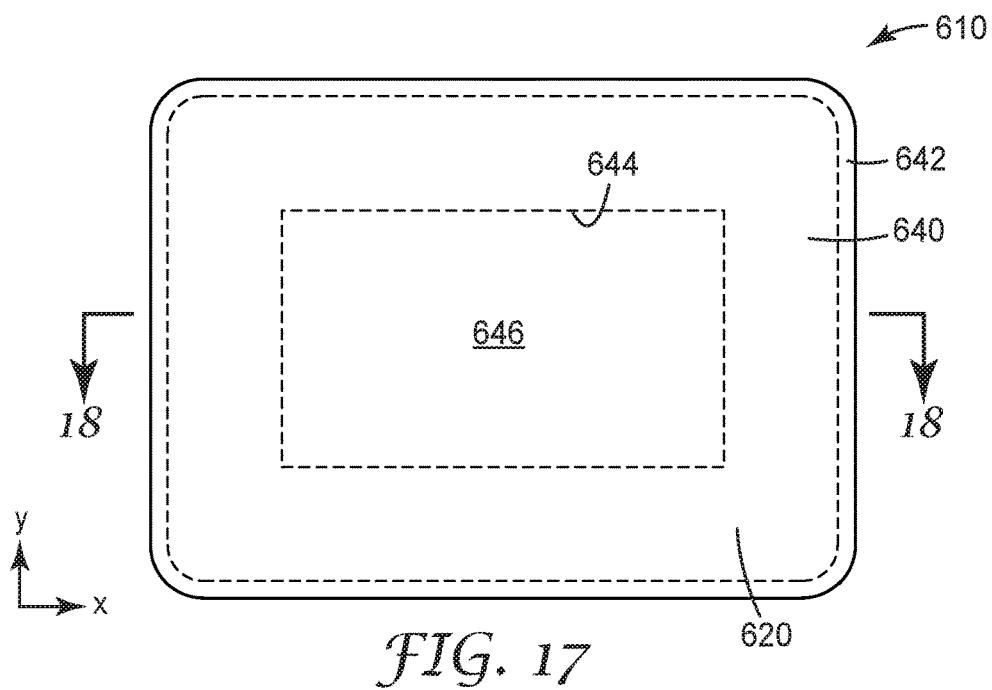
FIG. 17 depicts another illustrative embodiment of a shapeable article including a window opening formed in an interior of the shapeable member.
Figure 18:
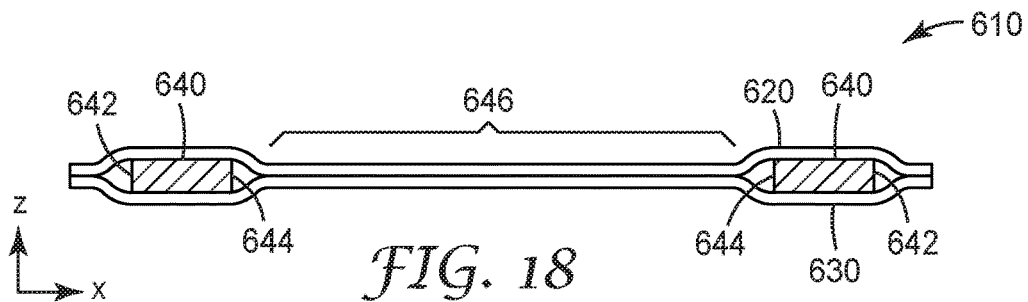
FIG. 18 is a cross-sectional view of the shapeable article of FIG. 17 taken along line 18-18 in FIG. 17.

Although in one or more embodiments, the shapeable members in shapeable articles as described herein may be completely continuous within their outer perimeters, one or more alternative embodiments may include shapeable members having one or more window openings formed within an outer perimeter. One illustrative example of a shapeable article 610 including a shapeable member 640 is depicted in FIGS. 17 and 18, where FIG. 18 is a cross-sectional view of shapeable article 610 taken along line 18-18 in FIG. 17. The shapeable article 610 includes coversheets 620 and 630 located on opposite sides of the shapeable member 640.

Coversheets 620 and 630 may be similar to any of the coversheets described in connection with other illustrative embodiments of shapeable articles as described herein. Similarly, shapeable member 640 may be constructed of components as discussed herein with respect to other shapeable members in other illustrative embodiments of shapeable articles as described herein.

The shapeable member 640 includes an outer perimeter 642 inset from an outer perimeter 616 of the shapeable article 610 such that the coversheets 620 and 630 form a border around the outer perimeter 642 of the shapeable member 640. In addition to outer perimeter 642 shapeable member 640 also includes an inner perimeter 644 defining a window opening 646 within the boundary of the outer perimeter 642 of the shapeable member 640.

Although shapeable member 640 includes only one window opening 646, one or more alternative embodiments of shapeable articles as described herein may include shapeable members having two or more separate window openings located within the boundary of the outer perimeter 642 of the shapeable member 640. Further, although the inner perimeter 644 and corresponding window opening 646 have a shape similar to the shape of the outer perimeter 642 of the shapeable member 640, window openings with shapes other than those of the outer perimeter 642 of shapeable member 640 may also be used in shapeable articles as described herein. In addition, the shape of the inner perimeter 644 and its corresponding window opening 646 are not required to be rectangular as depicted in FIG. 17, i.e., the inner perimeter 644 and its corresponding window opening 646 may take any selected shape.

Another optional feature depicted in connection with shapeable article 610 is that one or both of the coversheets 620 and 630 extend over the window opening 646 formed in the shapeable member 640. As a result, although the shapeable member 640 includes a window opening 646, the shapeable article 610 in which shapeable member 640 is located does not include a window opening because that opening is closed by one or more of the coversheets 620 and/or 630.

Figure 19:
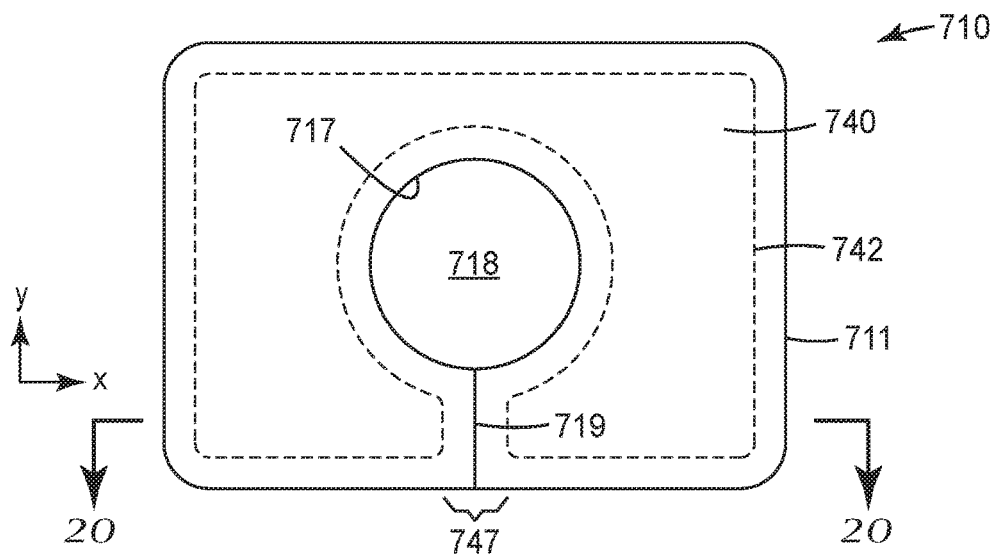
FIG. 19 depicts another illustrative embodiment of a shapeable article including a window opening and an access slit.
Figure 20:
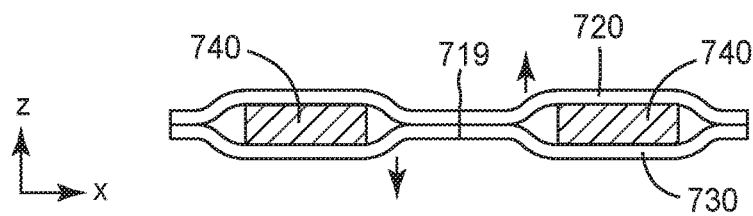
FIG. 20 is a cross-sectional view of the shapeable article of FIG. 19 taken along line 20-20 in FIG. 19.

Another illustrative embodiment of a shapeable article 710 including a shapeable member 740 is depicted in FIGS. 19 and 20, where FIG. 20 is a cross-sectional view of the shapeable article 710 taken along line 20-20 in FIG. 19. The shapeable article 710 includes a shapeable member 740 located between coversheets 720 and 730. In this illustrative embodiment, the coversheets 720 and 730 include an inner perimeter 717 defining a window opening 718 in the coversheets 720 and 730 in addition, the shapeable member 740 includes a perimeter 742 that follows the shape of the inner perimeter 717 such that the shapeable article 710 includes a window opening 718 formed through both the coversheets 720 and 730 as well as the shapeable member 740.

Another optional feature depicted in connection with the illustrative embodiment of shapeable article 710 is an access slit 719 formed through the coversheets 720 and 730 to allow access from an outer perimeter 711 of the shapeable article 710 to the window opening 718 defined by inner perimeter 717. In the illustrative embodiment depicted in FIGS. 19 and 20, the shapeable member 740 includes an outer perimeter 742 that follows outer perimeter 711 of the shapeable article 710, but extends inwardly on both sides of the access slit 719 where the outer perimeter 742 of the shapeable member 740 follows inner perimeter 717 defining window opening 718. As a result, the shapeable member 740 forms a gap 747 leading to window opening 718.

The access slit 719 formed through the coversheets 720 and 730 may be in the form of a cut line formed through the coversheets 720 and 730, with the coversheets 720 and 730 separated along the access slit 719. In one or more alternative embodiments, however, access slit 719 may be in the form of a row of perforations, a line of weakness, etc. along which coversheets 720 and 730 preferentially separate. In one or more embodiments, the shapeable article 710 can be manipulated on both sides of the access slit 719 to provide an opening through which tissues, organs, etc. can be inserted into the window opening 718. In one or more embodiments, manipulation of the shapeable article 710 in opposite directions on opposite sides of the access slit 719 as depicted by the arrows seen in FIG. 20 may be used to provide such an opening for access to the window opening 718.

Figure 21:
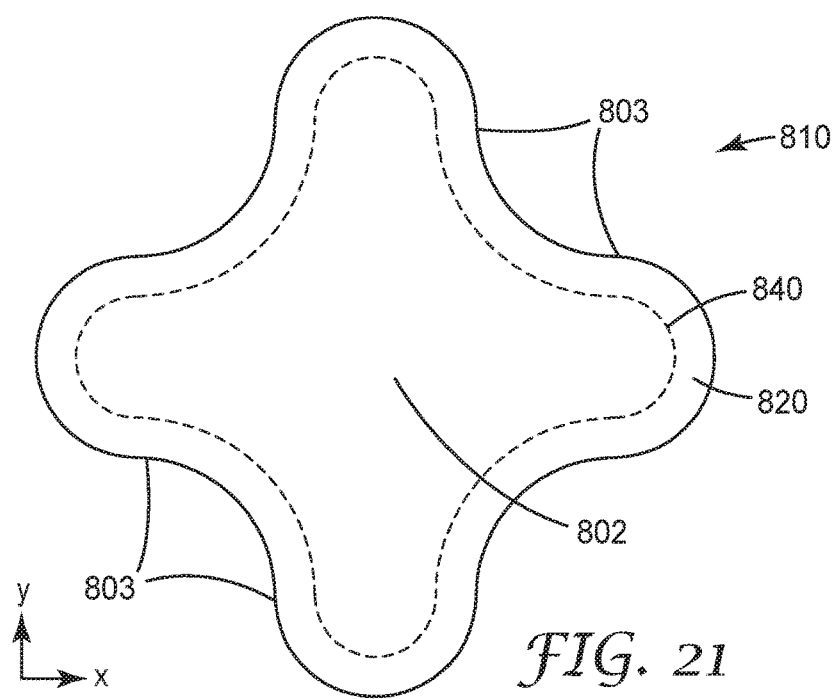
FIG. 21 depicts another illustrative embodiment of a shapeable article as described herein.

Although shapeable articles as described herein may often take the shape of a rectangle, shapeable articles may, in one or more alternative embodiments take a variety of different shapes, one of which is depicted in FIG. 21. The illustrative embodiment of shapeable article 810 is one example of a shapeable article having a nonrectangular shape. In particular, shapeable article 810 includes a central portion 802 with fingers 803 extending outward from the central portion 802. In one or more embodiments, the shapeable member 840 provided in the shapeable article 810 extends into each of the fingers 803 such that each of the fingers 803 can be manipulated into and maintain a non-planar shape along with central portion 802.

Figure 22:
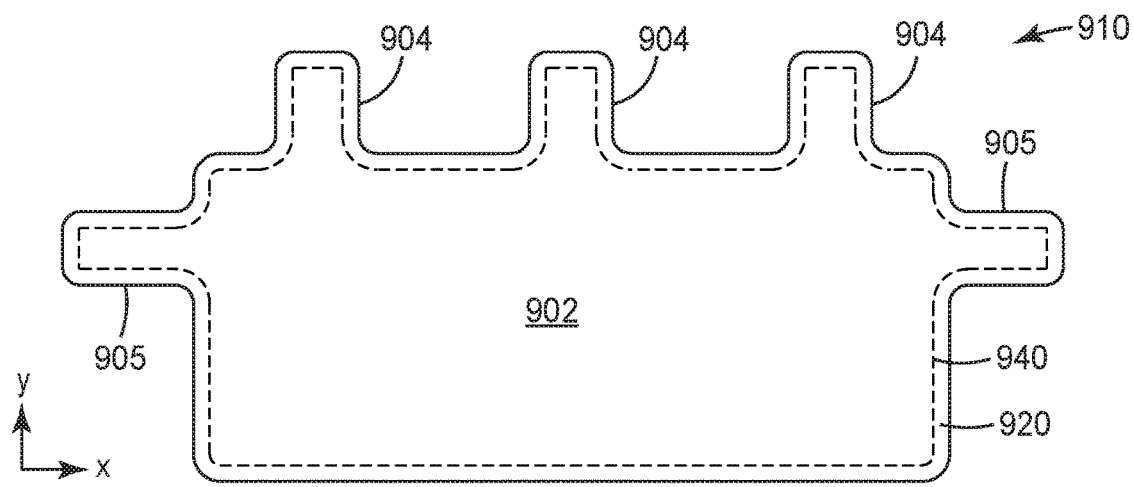
FIG. 22 depicts another illustrative embodiment of a shapeable article including tabs as described herein.

Another illustrative embodiment of a shapeable article as described herein is depicted in FIG. 22 where shapeable article 910 includes a shapeable member 940 located within a pair of coversheets, with only one coversheet 920 seen in the view of FIG. 22. Shapeable article 910 includes a central portion 902 in the general shape of a rectangle, while tabs 904 extend away from the generally rectangular central portion 902 along one side. Further, tabs 905 extend away from the generally rectangular central portion along opposite sides of the rectangular central portion 902. As seen in the shapeable article 910, tabs 904 and 905 which extend away from the generally rectangular central portion 902 do not occupy all of the side of the rectangular shape central portion from which they extend. In other words, the tabs 904 and 905 occupy less than all of the side from which they extend.

In the illustrative embodiment depicted in FIG. 22, the shapeable member 940 extends into the area defined by each of the tabs 904 and 905. In one or more alternative embodiments, however, the shapeable member may or may not extend into those tabs. Further, in one or more alternative embodiments the shapeable member may or may not occupy substantially all of the central portion 902 of the shapeable article 910 as depicted in FIG. 22. It should be understood that the arrangement of tabs 904 and 905 and shapeable article 910 provide only one example of an arrangement of tabs that may be provided on shapeable articles as described herein.

Figure 23:
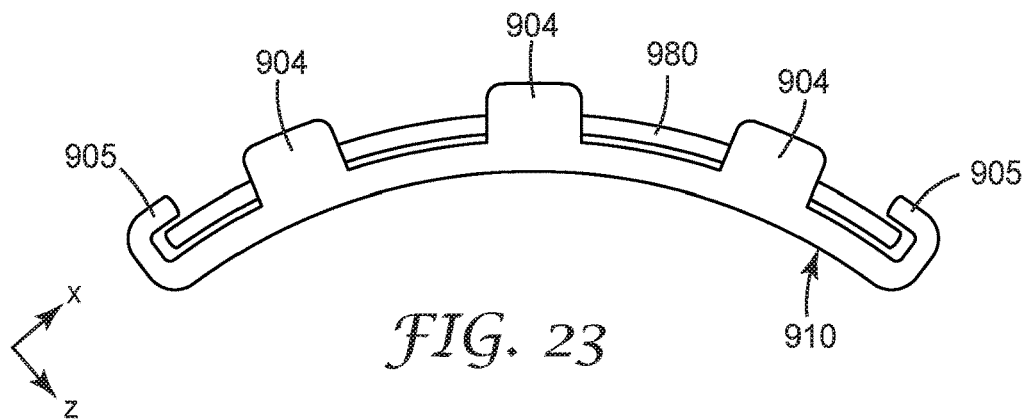
FIG. 23 depicts the illustrative embodiment of the shapeable article depicted in FIG. 22 attached to a structure such as a retractor plate.

Shapeable articles such as, e.g., illustrative embodiment of shapeable article 910, that include tabs may be well-suited for use in attaching the shapeable article 910 to other structures to assist in restraint of tissues and/or organs during surgical procedures. For example, the shapeable article 910 is depicted in FIG. 23 as being deployed on a curved retractor plate 980 which may be used in, for example, a BOOKWALTER retraction system. As depicted, the tabs 904 may be bent or manipulated over a top/bottom edge of the retractor plate 980 while tabs 905 may be bent or folded over a side edge of the retractor plate 980 such that shapeable article 910 may be retained in a selected position on the retractor plate 980.

Figure 24:
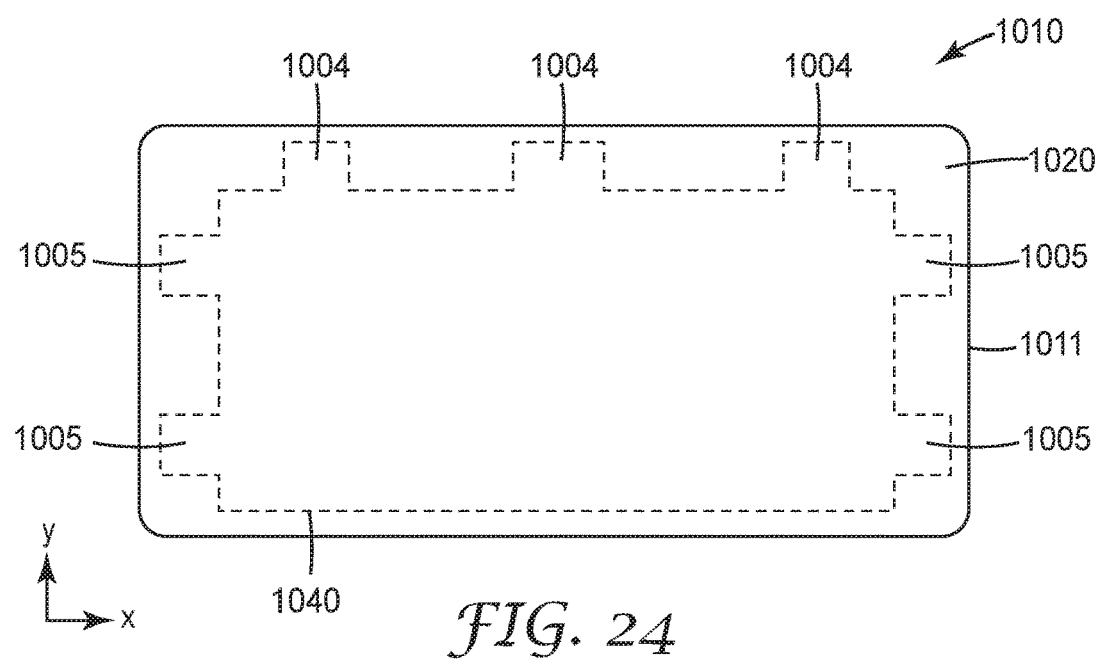
FIG. 24 depicts another illustrative embodiment of a shapeable article including tabs as described herein.

Still another illustrative embodiment of a shapeable article as described herein is depicted in FIG. 24 where shapeable article 1010 is depicted. Shapeable article 1010 includes coversheets attached to and containing a shapeable member 1040 as described herein in connection with other illustrative embodiments of shapeable articles (only one coversheet 1020 is visible in FIG. 24). The coversheets of shapeable article 1010 define an outer perimeter 1011 for the shapeable article that is, in the depicted illustrative embodiment, generally in the shape of a rectangle.

The shapeable member 1040 contained within the coversheets of the shapeable article 1010, however, has a different shape from the shape defined by the outer perimeter 1011. In particular, shapeable member 1040 includes a central section 1042 with tabs 1004 and 1005 extending outwardly from multiple sides of the central portion 1042 of the shapeable member 1040. In other words, although the shapeable article 1010 may be described as including tabs, those tabs do not protrude from an outer perimeter of the shapeable article 1010 as depicted above in connection with FIG. 22. Regardless, the tabs 1004 and 1005 of shapeable member 1040 in shapeable article 1010 may be used to assist in securing the shapeable article 1010 on other structures in a manner similar to that depicted in FIG. 30 in connection with shapeable article 910.

Shapeable article 1010 provides one example in which coversheets containing a shapeable member of a shapeable article define an article perimeter 1011, while the shapeable member 1040 located between the coversheets has a shapeable member perimeter, where the article perimeter and the shapeable member perimeter are different from each other. This is in contrast with, e.g., shapeable articles depicted in FIGS. 1, 17, 21, and 22 in which the article perimeters and the shapeable member perimeters have the same shape (although the member perimeter is typically inset from the article perimeter to allow for a border of coversheet material to encase the shapeable member located between coversheets).

Figure 25:
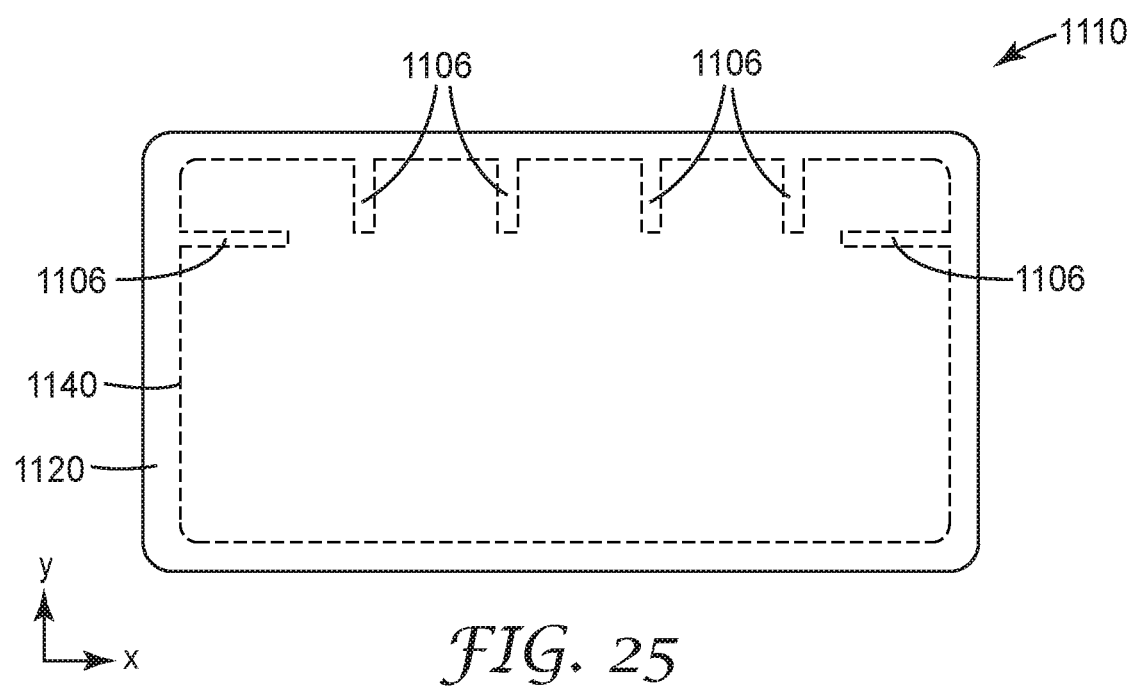
FIG. 25 depicts another illustrative embodiment of a shapeable article including slits as described herein.

Another illustrative embodiment of a shapeable article as described herein is depicted in FIG. 25. Shapeable article 1110 includes a shapeable member 1140 located between coversheets as discussed herein with respect to other illustrative embodiments of shapeable articles (with only one coversheet 1120 visible in the view of FIG. 25). The shapeable member 1140 includes one or more slits which, in the depicted embodiment, includes multiple slits 1106 that extend from an edge of the shapeable member 1140 inward toward a center of the shapeable member 1140. The slits may be provided to increase flexibility of the shapeable member around its perimeter.

Figure 26:
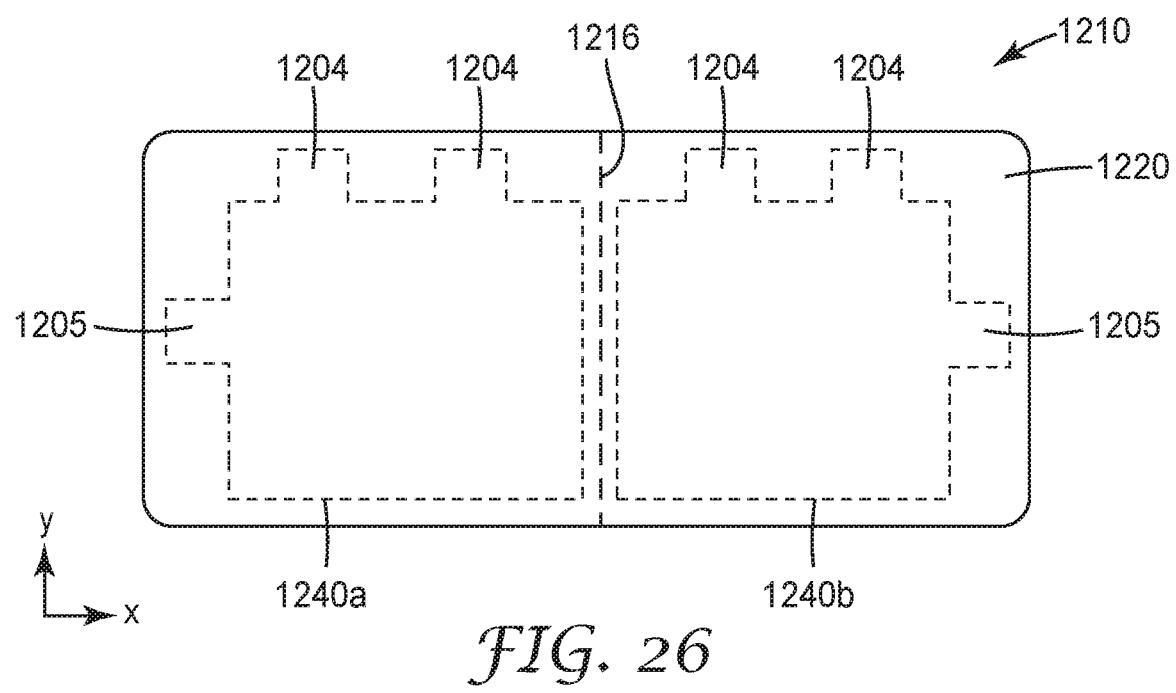
FIG. 26 depicts another illustrative embodiment of a shapeable article including two separate shapeable members and a line of separation in the coversheets located between the shapeable members as described herein.

Another illustrative embodiment of a shapeable article as described herein is depicted in FIG. 26. Shapeable article 1210 includes two shapeable members 1240a and 1240b located between coversheets (with only one coversheet 1220 visible in the view of FIG. 32). Each of the two shapeable members, which will be commonly referred to as shapeable members 1240, includes, in the depicted illustrative embodiment, tabs 1204 and 1205 extending outwardly from a central portion of each of the shapeable members 1240.

An additional feature depicted in connection with illustrative embodiment of shapeable member 1210 is a separation line 1216 that extends across the shapeable member 1210 between the shapeable members 1240. Separation line may be used to reduce the size of the shapeable article 1210 by allowing for separation of the coversheets along separation line 1216 while maintaining containment of the shapeable members 1240 between the coversheets after separation of the coversheets along separation line 1216. Separation line 1216 may be provided in a variety of forms, e.g., a plurality of perforations extending along line 1216, one or more lines of weakness in one or both of the coversheets containing separation line 1216, etc. In still other embodiments, separation line 1216 may merely be provided with printed or otherwise visible indicia indicating where a user may cut the coversheets without cutting or exposing the shapeable members 1240 located within the coversheets.

Although only one separation line 1216 and two shapeable members 1240 are depicted in the illustrative embodiment of shapeable article 1210, one or more alternative embodiments of shapeable articles as described herein may include two or more separation lines and a corresponding number of shapeable members (for example, a shapeable article including two separation lines may, in one or more embodiments, include three separate shapeable members located within the coversheets).

Figure 27:
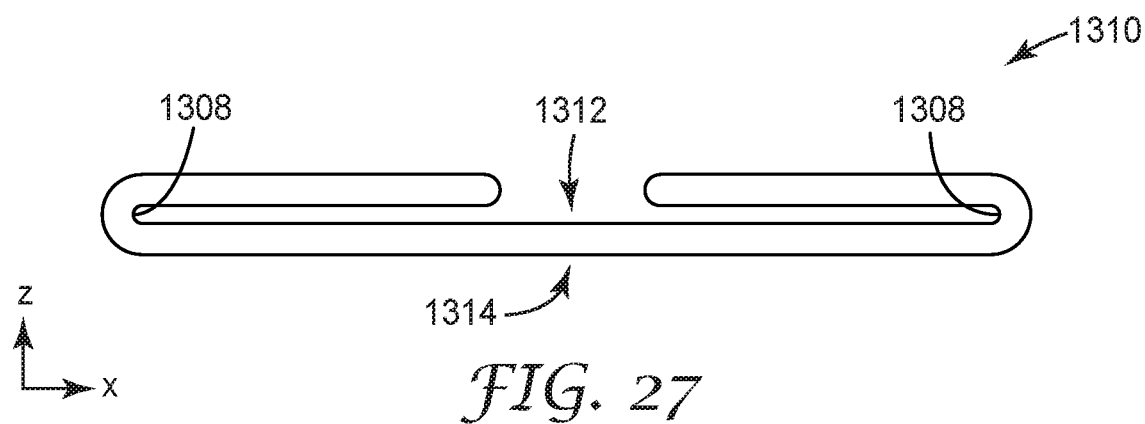
FIGS. 27-28 depict illustrative embodiments of shapeable articles including one or more folds as described herein.
Figure 28:
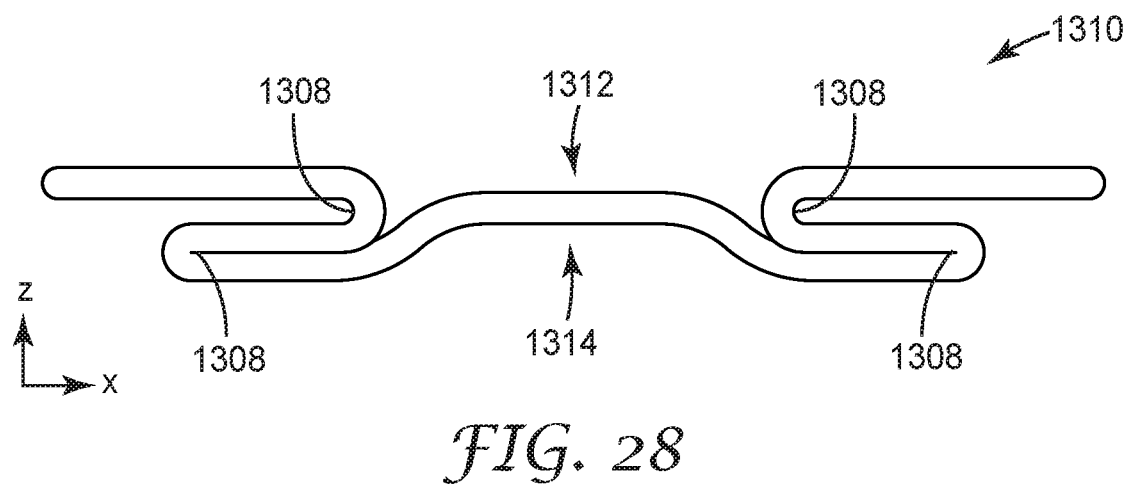

While illustrative embodiment of shapeable article 1210 depicted in FIG. 26 provides one example of a shapeable article that can be reduced in size using, e.g., separation line 1216, the illustrative embodiments of shapeable articles depicted in FIGS. 27 and 28 provide one example of features that may be provided to increase the size of a shapeable article.

In particular, shapeable article 1310 as depicted in FIG. 27 includes first and second major surfaces 1312 and 1314. The shapeable article 1310 also includes two fold lines 1308, with one or both of the fold lines 1308 providing for expansion of the first and second major surfaces 1312 and 1314 by unfolding of the shapeable article along one or both of the fold lines 1308. If, for example, fold-line 1308 on the right side of the shapeable article 1310 were unfolded, the size of the first and second major surfaces 1312 and 1314 would be increased because more of the shapeable article 1310 would be facing both upward and downward in the view depicted in FIG. 27.

Another illustrative embodiment of shapeable article 1310 as depicted in FIG. 28 provides a different set of fold lines that may be used to increase the size of the first and second major surfaces 1312 and 1314 of the shapeable article 1310. In particular, shapeable article 1310 includes multiple fold lines 1308. In one or more embodiments, one or more of these fold lines may be unfolded to increase the size of the first and second major surfaces 1312 and 1314. Unfolding of this embodiment may potentially be achieved by, e.g., placing the shapeable article in tension along the X direction.

The shapeable articles as described herein may be used in a variety of surgical procedures to restrain tissues and/or organs from entering or leaving a selected area. In one or more embodiments, the shapeable articles as described herein may be combined by folding and/or interlocking complementary features found on two or more of the shapeable articles as described herein.

Figure 29:
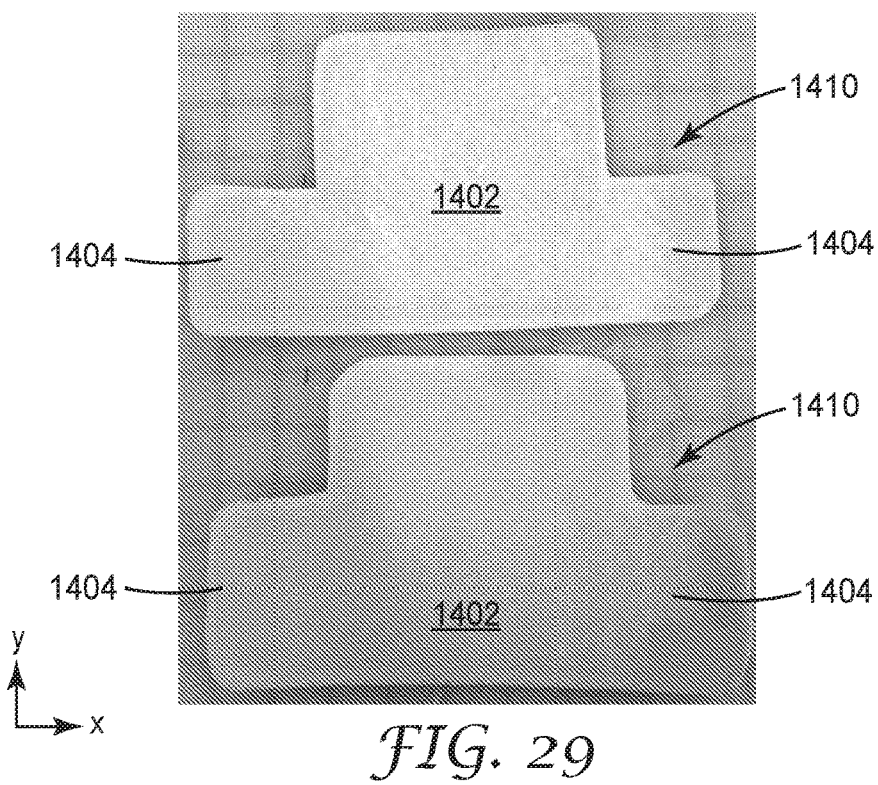
FIG. 29 depicts illustrative embodiments of shapeable articles including tabs as described herein.

FIG. 29 depicts one illustrative embodiment of shapeable articles 1410 that may be used together in a manner that helps to define an area from which tissue and/or organs may be restricted from entering or leaving. Each of the shapeable articles 1410 includes a central portion 1402 and a pair of tabs 1404 extending away from the central portion on opposite sides of central portion 1402 of the shapeable article 1410.

Figure 30:
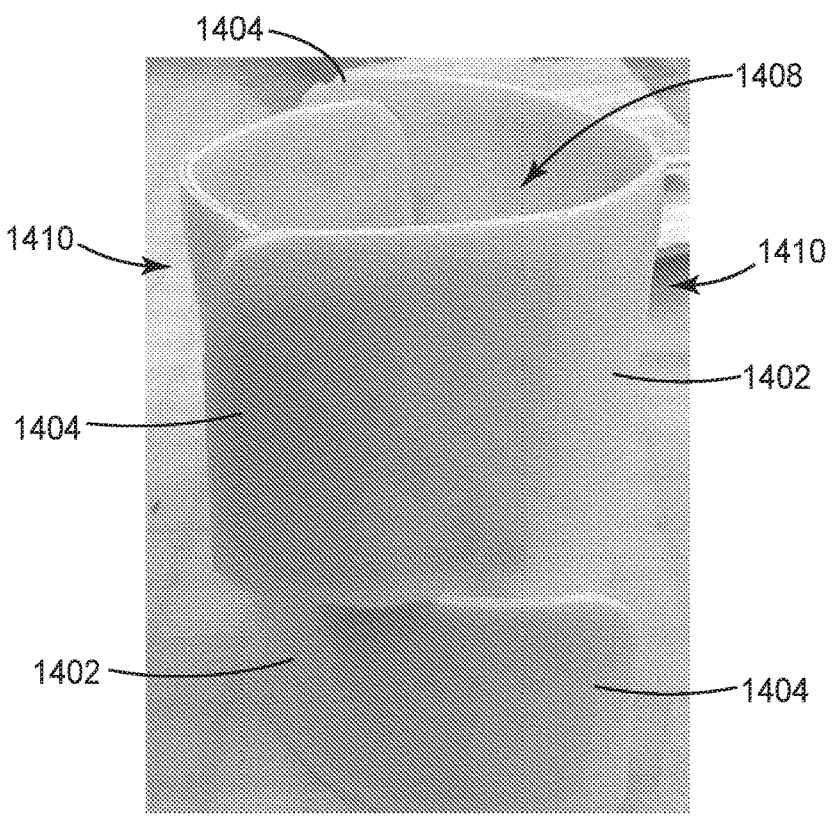
FIG. 30 is a perspective view of the shapeable articles of FIG. 29 arranged in an interlocking relationship.

As seen in FIG. 30, the two shapeable articles 1410 depicted in FIG. 29 have been manipulated into arcuate shapes and arranged such that tabs 1404 on opposing shapeable articles 1410 overlap with the central portions 1402 of the opposing shapeable article 1410 to form a loosely interlocking relationship defining an area or passage 1408 between the central portions 1402 of the pair of shapeable articles 1410. Tissues and/or organs may be restricted from entering or leaving area or passage 1408 when the pair of shapeable articles 1410 depicted in FIG. 30 are used in a surgical procedure.

Figure 31:
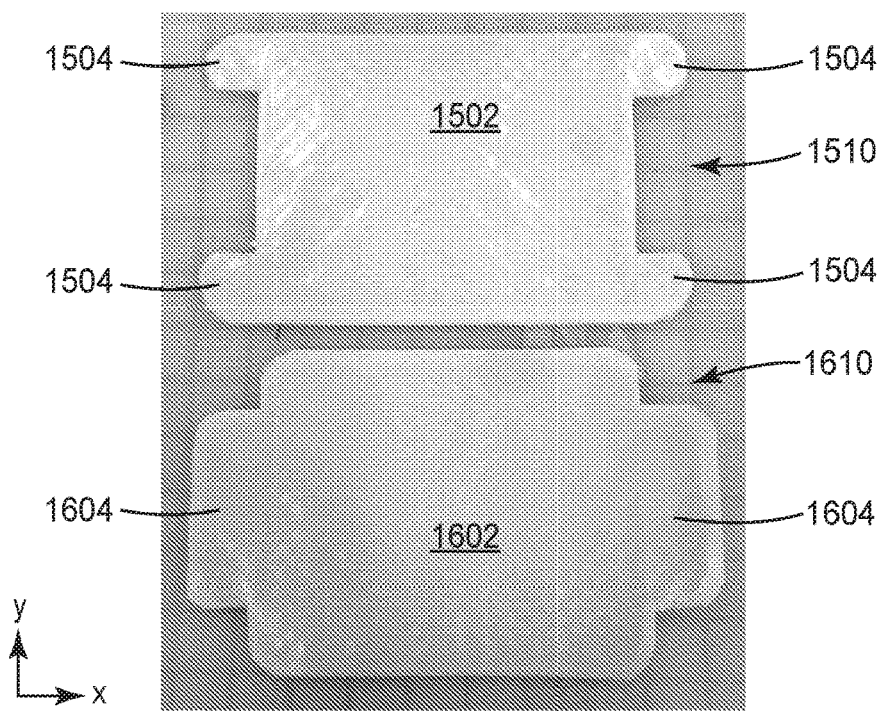
FIG. 31 depicts illustrative embodiments of shapeable articles including tabs as described herein.

FIG. 31 depicts another illustrative embodiment of two different shapeable articles 1510 and 1610 that may be used together in a manner to help define an area or passage. Shapeable article 1510 includes a central portion 1502 with a pair of tabs 1504 extending from two sides of the generally rectangular central portion. Shapeable article 1610 includes a generally rectangular central portion 1602 with a single tab extending from each of the two opposing edges of the generally rectangular central portion 1602.

In one or more embodiments, the tabs 1504 extending from one edge of the shapeable article 1510 may be separated from each other by a distance that corresponds generally to the length of tab 1604 extending from one edge of shapeable article 1610. As a result, at least some mechanical interference may be achieved when tab 1604 on shapeable article 1610 is positioned between tabs 1504 on shapeable article 1510. Mechanical interference between tab 1604 and pair of tabs 1504 may be enhanced where, for example, the length of tab 1604 on shapeable article 1610 is equal to or greater than the distance between the pair of tabs 1504 on shapeable article 1510.

Figure 32:
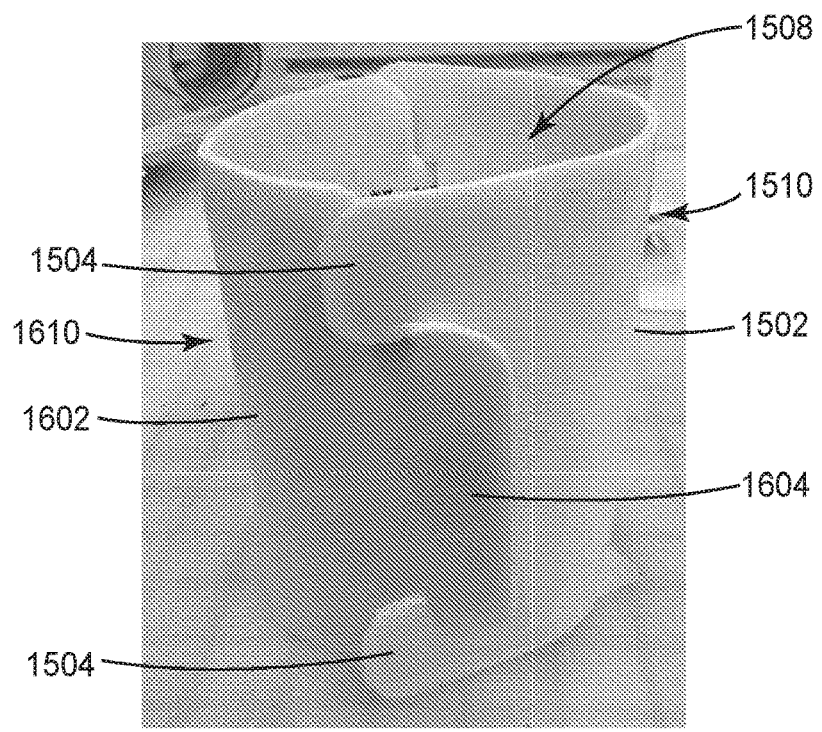
FIG. 32 is a perspective view of the shapeable articles of FIG. 31 arranged in an interlocking relationship.

As seen in FIG. 32, the two shapeable articles 1510 and 1610 depicted in FIG. 31 have been manipulated into arcuate shapes and arranged such that each of tabs 1604 on shapeable article 1610 is positioned between a pair of tabs 1504 on shapeable article 1510. The pair of shapeable articles 1510 and 1610, when so manipulated and arranged, may provide an area or passage 1508 between their respective central portions 1502 and 1602. Tissues and/or organs may be restricted from entering or leaving the area or passage when the pair of shapeable articles 1510 and 1610 depicted in FIG. 32 are used in a surgical procedure.

Figure 33:
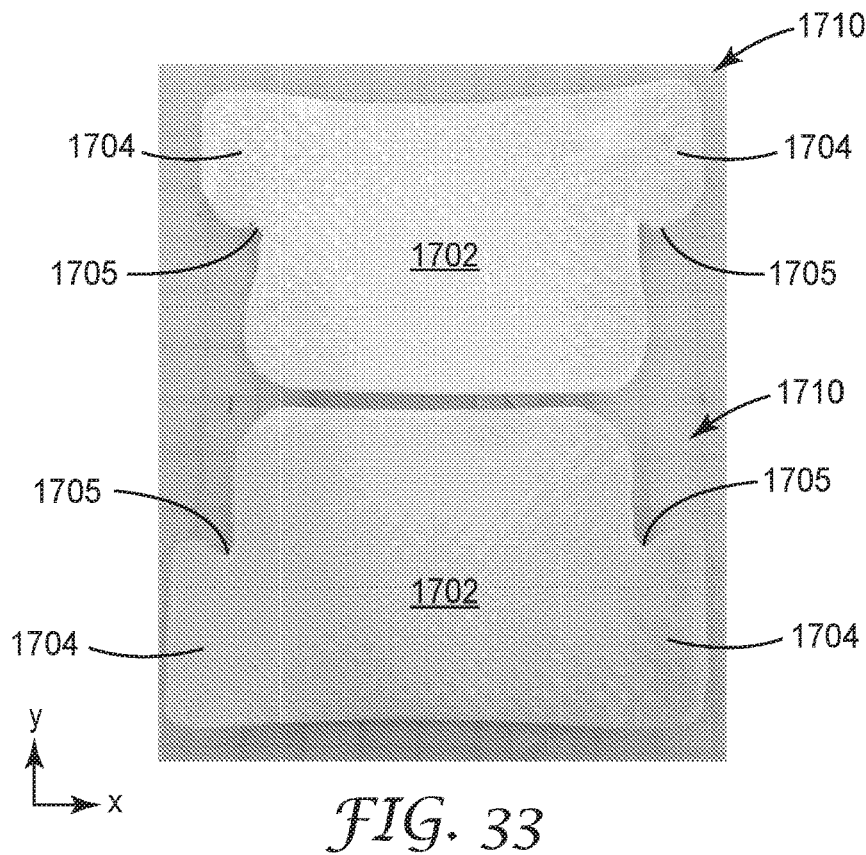
FIG. 33 depicts illustrative embodiments of shapeable articles including tabs as described herein.

FIG. 33 depicts another illustrative embodiment of a shapeable article 1710 that may be used in groups of two or more to define an area or passage from which, e.g., tissues and/or organs may be restricted from entering or leaving during a surgical procedure. In particular, the shapeable articles 1710 include a central portion 1702 with tabs 1704 extending from opposing edges of the shapeable article 1710. An additional feature depicted in connection with shapeable article 1710 are notches 1705 formed at a junction of the tabs 1704 on the intermediate end of the tabs 1704 (i.e., the end of the tabs 1704 located between opposing edges of the central portion 1702 rather than at a corner of the shapeable article 1710).

Figure 34:
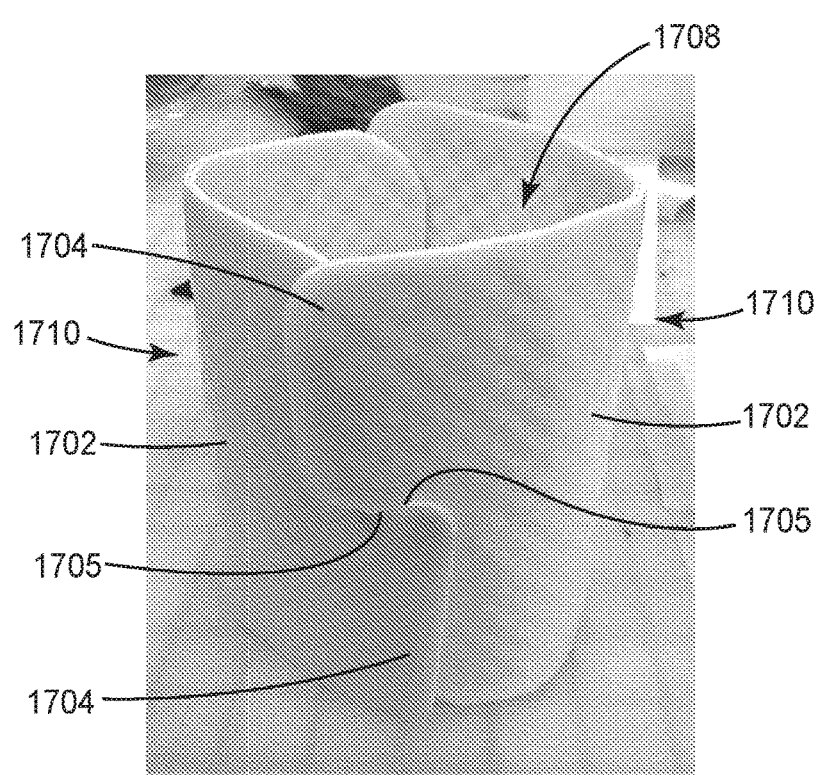
FIG. 34 is a perspective view of the shapeable articles of FIG. 33 arranged in an interlocking relationship.

As seen in FIG. 34, the two shapeable articles 1710 depicted in FIG. 33 have been manipulated into arcuate shapes and arranged such that tabs 1704 on opposing shapeable articles 1710 overlap with the central portions 1702 of the opposing shapeable article 1710. The interlocking relationship between the pairs of tabs 1704 on the opposing shapeable articles 1710 is enhanced by the complementary notches 1705 located on the intermediate ends of the tabs 1704 and may, in one or more embodiments, provide more resistance to disengagement of the shapeable article 1710 from each other during use. The opposing shapeable article 1710, when arranged and interconnected as seen in FIG. 34, define an area or passage 1708 between the shapeable article 1710 from which tissues and/or organs may be restricted from entering or leaving when the pair of shapeable articles 1710 are used in a surgical procedure.

Figure 35:
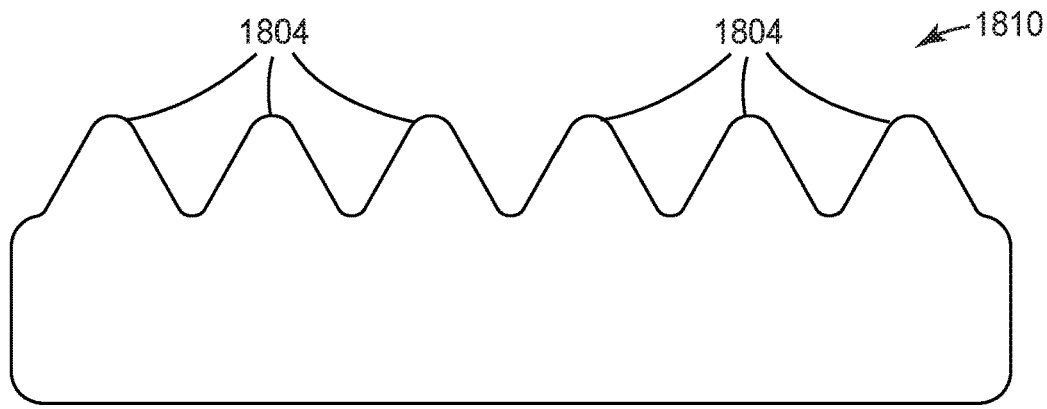
FIG. 35 depicts another illustrative embodiment of a shapeable article including tabs as described herein.

FIG. 35 depicts another illustrative embodiment of a shapeable article 1810 that may be used to define an area or passage from which, e.g., tissues and/or organs may be restricted from entering or leaving during a surgical procedure. In particular, the shapeable articles 1810 includes a central portion 1802 with tabs 1804 extending from an edge of the shapeable article 1810.

Figure 36:
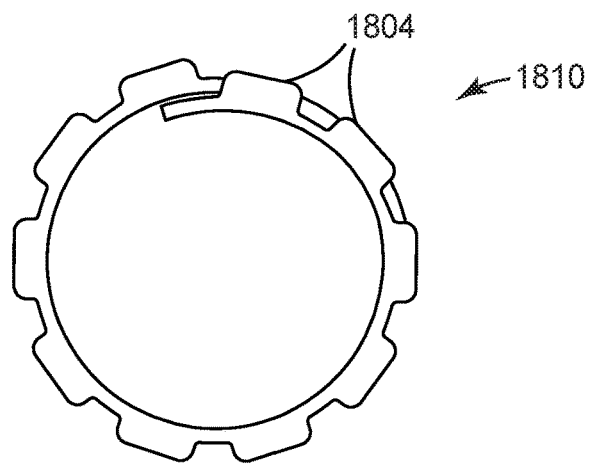
FIG. 36 is a perspective view of the shapeable article of FIG. 35 arranged in an interlocking relationship.

As seen in FIG. 36, the shapeable article 1810 depicted in a flat configuration in FIG. 35 has been manipulated into an arcuate shape and arranged such that tabs 1804 on the shapeable article 1810 overlap with the central portion 1802 to assist in holding the arcuate shape of the 1810 as depicted in FIG. 36. Alternatively, the tabs 1804 may be bent over the edge of an incision and/or other retraction devices (e.g., retraction plates in a table-mounted retraction system, etc.).

Although some illustrative embodiments of shapeable articles as described herein rely on folding or bending of a shapeable member located in the shapeable article as discussed in connection with, e.g., FIG. 23 or mechanical interference between two shapeable articles to retain a shape or position as discussed in connection with, e.g., FIGS. 29-34, or mechanical interference caused by folding of one shapeable article as discussed in connection with FIGS. 35-36, one or more embodiments of shapeable articles as described herein may include other components that may be used to assist in attaching the shapeable articles to other structures and/or surfaces (e.g., retractor plates, surgical drapes, incise drapes, wound edge protectors, patient's skin, etc.) and/or to each other/themselves. In particular, one or more embodiments of shapeable articles as described herein may include pressure sensitive adhesives located on at least a portion of an exterior surface of the shapeable article, cohesive materials on at least a portion of an exterior surface of the shapeable article, mechanical fasteners (e.g., hook and loop fasteners, stem fasteners (e.g., 3M DUAL LOCK reclosable stem fasteners), magnets, etc.

Figure 37:
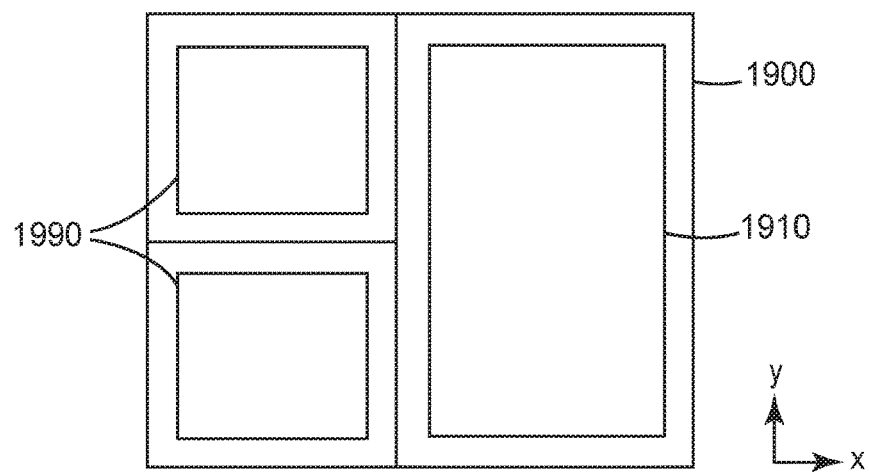
FIG. 37 is a schematic diagram of one illustrative embodiment of a kit that may include one or more shapeable articles as described herein along with other items in a sealed package.

One or more of the shapeable articles described herein may be provided in a kit along with one or more other items. FIG. 37 is a schematic diagram of one illustrative kit that includes at least one shapeable article 1910 as described herein along with other articles such as e.g. lap sponges 1990. All of the components of the kit may be contained within a package 1900 which may, in one or more embodiments, be a sealed package, with the articles located therein being sterilized for use in a surgical procedure. In still other embodiments, the package 1900 may be a frangible sealed package containing sterilized items such as one or more shapeable articles 1910 and one or more lap sponges 1990.

ILLUSTRATIVE EMBODIMENTS

Embodiment 1

A manually shapeable article comprising: a shapeable member comprising a first sheet comprising a first major surface and a second major surface, wherein the first major surface and the second major surface are on opposite sides of the first sheet, wherein the first sheet further comprises a land portion extending between and connecting a plurality of structured elements, wherein each structured element of the plurality of structured elements comprises a protrusion extending from the land portion on the first major surface of the first sheet; optionally, a second sheet comprising a first major surface and a second major surface, wherein the first major surface and the second major surface are on opposite sides of the second sheet, wherein the second sheet further comprises a land portion extending between and connecting a plurality of structured elements, wherein each structured element of the plurality of structured elements comprises a protrusion extending from the land portion on the first major surface of the second sheet; wherein the first sheet is attached the second sheet such that the second major surface of the first sheet faces the first or second major surface of the second sheet; a first coversheet attached to a first major surface of the shapeable member; and a second coversheet attached to a second major surface of the shapeable member.

Embodiment 2

An article according to embodiment 1, wherein each structured element of the first sheet comprises a depression on the second major surface that corresponds to the protrusion extending from the first major surface of the first sheet.

Embodiment 3

An article according to any one of embodiments 1 to 2, wherein each structured element of the second sheet comprises a depression on the second major surface that corresponds to each protrusion extending from the first major surface of the second sheet.

Embodiment 4

An article according to embodiment 1, wherein each structured element of the first sheet comprises a depression on the second major surface that corresponds to the protrusion extending from the first major surface of the first sheet; wherein each structured element of the second sheet comprises a depression on the second major surface that corresponds to each protrusion extending from the first major surface of the second sheet; and wherein the first sheet is attached the second sheet such that the second major surface of the first sheet faces the second major surface of the second sheet.

Embodiment 5

An article according to embodiment 1, wherein each structured element of the first sheet comprises a depression on the second major surface that corresponds to the protrusion extending from the first major surface of the first sheet; wherein each structured element of the second sheet comprises a depression on the second major surface that corresponds to each protrusion extending from the first major surface of the second sheet; and wherein the first sheet is attached the second sheet such that the second major surface of the first sheet faces the first major surface of the second sheet.

Embodiment 6

An article according to embodiment 1, wherein the plurality of structured elements on the first sheet are aligned with the plurality of structured elements on the second sheet.

Embodiment 7

An article according to any one of embodiments 1 to 6, wherein the land portion between the plurality of structured elements on the first sheet is aligned with the land portion between the plurality of structured elements on the second sheet.

Embodiment 8

An article according to any one of embodiments 1 to 7, wherein the land portion between the plurality of structured elements on the first sheet is attached to the land portion between the plurality of structured elements on the second sheet.

Embodiment 9

An article according to any one of embodiments 1 to 7, wherein the land portion between the plurality of structured elements on the first sheet is adhesively attached to the land portion between the plurality of structured elements on the second sheet.

Embodiment 10

An article according to any one of embodiments 1 to 7, wherein the land portion between the plurality of structured elements on the first sheet is welded to the land portion between the plurality of structured elements on the second sheet.

Embodiment 11

An article according to any one of embodiments 1 to 10, wherein all of the structured elements of the plurality of structured elements of the first sheet are separated from each other by the land portion of the first sheet.

Embodiment 12

An article according to any one of embodiments 1 to 10, wherein all of the structured elements of the plurality of structured elements of the second sheet are separated from each other by the land portion of the second sheet.

Embodiment 13

An article according to any one of embodiments 1 to 12, wherein the land portion occupies 15% or more of a projection of the first major surface of the first sheet when the first major surface is flat and projected onto a plane.

Embodiment 14

An article according to any one of embodiments 1 to 13, wherein the land portion occupies 70% or less of a projection of the first major surface of the first sheet when the first major surface is flat and projected onto a plane.

Embodiment 15

An article according to any one of embodiments 1 to 14, wherein the plurality of structured elements occupy 15% or more of a projection of the first major surface of the first sheet when the first major surface is flat and projected onto a plane.

Embodiment 16

An article according to any one of embodiments 1 to 15, wherein the plurality of structured elements occupy 70% or less of a projection of the first major surface of the first sheet when the first major surface is flat and projected onto a plane.

Embodiment 17

An article according to any one of embodiments 1 to 16, wherein all of the structured elements of the plurality of structured elements on the first sheet have the same shape.

Embodiment 18

An article according to embodiment 17, wherein all of the structured elements of the plurality of structured elements in the second sheet have the same shape.

Embodiment 19

An article according to any one of embodiments 17 to 18, wherein all of the structured elements of the plurality of structured elements on the first sheet have the same size.

Embodiment 20

An article according to embodiment 19, wherein all of the structured elements of the plurality of structured elements in the second sheet have the same size.

Embodiment 21

An article according to any one of embodiments 1 to 16, wherein two or more of the structured elements of the plurality of structured elements on the first sheet have different shapes.

Embodiment 22

An article according to embodiment 21, wherein two or more of the structured elements of the plurality of structured elements on the second sheet have different shapes.

Embodiment 23

An article according to any one of embodiments 1 to 22, wherein the plurality of structured elements on the first sheet are arranged in a uniformly spaced array.

Embodiment 24

An article according to any one of embodiments 1 to 23, wherein the plurality of structured elements in the second sheet are arranged in a uniformly spaced array.

Embodiment 25

An article according to any one of embodiments 1 to 24, wherein each structured element of the plurality of structured elements on the first sheet comprises a maximum cross-sheet dimension of 2.5 centimeters or less when the land portion of the second major surface of the first sheet is in a flat configuration.

Embodiment 26

An article according to any one of embodiments 1 to 24, wherein each structured element of the plurality of structured elements on the first sheet comprises a maximum cross-sheet dimension of 1 centimeter or less when the land portion of the second major surface of the first sheet is in a flat configuration.

Embodiment 27

An article according to any one of embodiments 1 to 26, wherein each structured element of the plurality of structured elements on the second sheet comprises a maximum cross-sheet dimension of 2.5 centimeters or less when the land portion of the second major surface of the second sheet is in a flat configuration.

Embodiment 28

An article according to any one of embodiments 1 to 26, wherein each structured element of the plurality of structured elements on the second sheet comprises a maximum cross-sheet dimension of 1 centimeter or less when the land portion of the second major surface of the second sheet is in a flat configuration.

Embodiment 29

An article according to any one of embodiments 1 to 28, wherein the structured elements of two or more neighboring structured element pairs of the plurality of structured elements on the first sheet are separated from each other by the land portion of the first sheet by a maximum inter-element distance 2.5 centimeters or less when the land portion of the second major surface of the first sheet is in a flat configuration.

Embodiment 30

An article according to any one of embodiments 1 to 28, wherein the structured elements of two or more neighboring structured element pairs of the plurality of structured elements on the first sheet are separated from each other by the land portion of the first sheet by a maximum inter-element distance 1 centimeter or less when the land portion of the second major surface of the first sheet is in a flat configuration.

Embodiment 31

An article according to any one of embodiments 1 to 30, wherein the structured elements of two or more neighboring structured element pairs of the plurality of structured elements on the second sheet are separated from each other by the land portion of the second sheet by a maximum inter-element distance of 2.5 centimeters or less when the land portion of the second major surface of the second sheet is in a flat configuration.

Embodiment 32

An article according to any one of embodiments 1 to 30, wherein the structured elements of two or more neighboring structured element pairs of the plurality of structured elements on the second sheet are separated from each other by the land portion of the second sheet by a maximum inter-element distance of 1 centimeter or less when the land portion of the second major surface of the second sheet is in a flat configuration.

Embodiment 33

An article according to any one of embodiments 1 to 32, wherein the protrusion of each structured element of the plurality of structured elements of the first sheet comprises a height measured from the land portion on the second major surface surrounding the structured element when the land portion of the second major surface of the first sheet is in a flat configuration, and wherein the height 2 centimeters or less.

Embodiment 34

An article according to embodiment 33, wherein the height is greater than zero.

Embodiment 35

An article according to any one of embodiments 1 to 34, wherein the first sheet comprises a metal foil.

Embodiment 36

An article according to any one of embodiments 1 to 34, wherein the first sheet comprises a polymeric sheet comprising the land portions and the plurality of structured elements.

Embodiment 37

An article according to any one of embodiments 1 to 34, wherein the first sheet consists essentially of a polymeric sheet comprising the land portions and the plurality of structured elements.

Embodiment 38

An article according to any one of embodiments 1 to 37, wherein the second sheet comprises a metal foil.

Embodiment 39

An article according to any one of embodiments 1 to 37, wherein the second sheet comprises a polymeric sheet comprising the land portions and the plurality of structured elements.

Embodiment 40

An article according to any one of embodiments 1 to 37, wherein the second sheet consists essentially of a polymeric sheet comprising the land portions and the plurality of structured elements.

Embodiment 41

An article according to any one of embodiments 1 to 40, wherein the protrusion of each structured element of the plurality of structured elements comprises a spherical dome-shaped protrusion.

Embodiment 42

An article according to any one of embodiments 1 to 41, wherein the protrusion of each structured element of the plurality of structured elements comprises a non-circular shape at a junction defined by the protrusion and the land portion surrounding the protrusion.

Embodiment 43

An article according to any one of embodiments 1 to 42, wherein the first coversheet and the second coversheet comprise a monolithic border about the perimeter of the shapeable member.

Embodiment 44

An article according to any one of embodiments 1 to 42, wherein the first coversheet is attached to the second coversheet about a perimeter of the shapeable member.

Embodiment 45

An article according to embodiment 44, wherein the first coversheet and the second coversheet are adhesively attached to each other about the perimeter of the shapeable member.

Embodiment 46

An article according to embodiment 44, wherein the first coversheet and the second coversheet are chemically or thermally welded to each other about the perimeter of the shapeable member.

Embodiment 47

An article according to any one of embodiments 1 to 46, wherein the first coversheet is attached to only a portion of the first major surface of the first sheet.

Embodiment 48

An article according to embodiment 47, wherein the first coversheet is attached to the protrusions of the plurality of structured elements on the first major surface of the first sheet.

Embodiment 49

An article according to embodiment 47, wherein the first coversheet is attached to only a portion of the protrusion of each structured element on the first sheet.

Embodiment 50

An article according to any one of embodiments 47 to 49, wherein the first coversheet is not attached to the land portion on the first major surface of the first sheet.

Embodiment 51

An article according to any one of embodiments 47 to 50, wherein the first coversheet is adhesively attached to the first sheet.

Embodiment 52

An article according to any one of embodiments 1 to 51, wherein the second coversheet is attached to only a portion of the first major surface of the second sheet.

Embodiment 53

An article according to embodiment 52, wherein the second coversheet is attached to the protrusions of the plurality of structured elements on the first major surface of the second sheet.

Embodiment 54

An article according to embodiment 52, wherein the second coversheet is attached to only a portion of the protrusion of each structured element on the second sheet.

Embodiment 55

An article according to any one of embodiments 52 to 54, wherein the second coversheet is not attached to the land portion on the first major surface of the second sheet.

Embodiment 56

An article according to any one of embodiments 52 to 55, wherein the second coversheet is adhesively attached to the second sheet

Embodiment 57

An article according to any one of embodiments 1 to 56, wherein the first coversheet exhibits tensile elongation greater than zero and 1000% or less.

Embodiment 58

An article according to any one of embodiments 1 to 57, wherein the first coversheet comprises one or more layers selected from a foam layer, a polymeric film, a nonwoven sheet, a woven sheet, a knitted sheet, a mesh sheet, and a net sheet.

Embodiment 59

An article according to any one of embodiments 1 to 58, wherein the first coversheet comprises a compressible layer.

Embodiment 60

An article according to embodiment 59, wherein the compressible layer comprises closed cell foam.

Embodiment 61

An article according to any one of embodiments 59 to 60, wherein the compressible layer exhibits compression set of 50% or less of an original thickness when tested according to ASTM D3575.

Embodiment 62

An article according to any one of embodiments 1 to 61, wherein the second coversheet exhibits tensile elongation greater than zero and 1000% or less.

Embodiment 63

An article according to any one of embodiments 1 to 62, wherein the second coversheet comprises one or more layers selected from a foam layer, a polymeric film, a nonwoven sheet, a woven sheet, a knitted sheet, a mesh sheet, and a net sheet.

Embodiment 64

An article according to any one of embodiments 1 to 63, wherein the second coversheet comprises a compressible layer.

Embodiment 65

An article according to embodiment 64, wherein the compressible layer of the second coversheet comprises closed cell foam.

Embodiment 66

An article according to any one of embodiments 64 to 65, wherein the compressible layer of the second coversheet exhibits compression set of 50% or less of an original thickness when tested according to ASTM D3575.

Embodiment 67

An article according to any one of embodiments 1 to 66, wherein the article comprises a perimeter in the general shape of a rectangle, with one or more tabs extending outward from at least one side of the rectangular, wherein each tab of the one or more tabs occupies less than all of the side from which it extends.

Embodiment 68

An article according to embodiment 67, wherein the shapeable member extends into the area defined the one or more tabs.

Embodiment 69

An article according to any one of embodiments 1 to 66, wherein the article comprises non-rectangular shape comprising a central portion and two or more fingers extending outwardly from the central portion, wherein the shapeable member extends into each finger of the two or more fingers.

Embodiment 70

An article according to any one of embodiments 1 to 66, wherein the first coversheet and the second coversheet define an article perimeter having an article shape, and wherein the shapeable member located between the first coversheet and the second coversheet comprises a member perimeter defining a member shape that is different than the article shape.

Embodiment 71

An article according to any one of embodiments 1 to 66, wherein the first coversheet and the second coversheet define an article perimeter having an article shape, and wherein the shapeable member located between the first coversheet and the second coversheet comprises a member perimeter defining a member shape that is the same as the article shape.

Embodiment 72

An article according to any one of embodiments 1 to 71, wherein the shapeable member comprises one or more slits formed through the shapeable member, wherein each slit of the one or more slits extends from an edge of the shapeable member inward toward a center of the shapeable member.

Embodiment 73

An article according to any one of embodiments 1 to 66, wherein the first coversheet and the second coversheet define an article perimeter having a generally rectangular shape, and wherein the shapeable member located between the first coversheet and the second coversheet comprises a member perimeter defining a non-rectangular member shape that is different than the generally rectangular shape of the article perimeter.

Embodiment 74

An article according to embodiment 73, wherein the non-rectangular member shape comprises a generally rectangular shape comprising one or more tabs extending outward from at least one side of the rectangular, wherein each tab of the one or more tabs occupies less than all of the side from which it extends.

Embodiment 75

An article according to any one of embodiments 1 to 74, wherein the shapeable member comprises a window opening formed therein, wherein the shapeable member forms a frame around the window opening.

Embodiment 76

An article according to embodiment 75, wherein the first coversheet and the second coversheet extend over the window opening formed in the shapeable member.

Embodiment 77

An article according to any one of embodiments 1 to 76, wherein the article comprises a stiffness of 100 N or less according to a three-point bend test.

Embodiment 78

An article according to any one of embodiments 1 to 77, wherein the first coversheet comprises an outer surface facing away from the shapeable member, and wherein the outer surface comprises a copolymer composition having a mean coefficient of friction of at least 0.2.

Embodiment 79

An article according to any one of embodiments 1 to 77, wherein the first coversheet comprises an outer surface facing away from the shapeable member, and wherein the outer surface comprises a copolymer composition having a mean coefficient of friction of up to 0.45.

Embodiment 80

An article according to embodiment 79, wherein the mean coefficient of friction of the copolymer composition is at least 0.2.

Embodiment 81

An article according to any one of embodiments 78 to 80, wherein the mean coefficient of friction of the copolymer composition is up to 0.35.

Embodiment 82

An article according to any one of embodiments 1 to 81, wherein the second coversheet comprises an outer surface facing away from the shapeable member, and wherein the outer surface of the second coversheet comprises a copolymer composition having a mean coefficient of friction of at least 0.2.

Embodiment 83

An article according to any one of embodiments 1 to 81, wherein the second coversheet comprises an outer surface facing away from the shapeable member, and wherein the outer surface of the second coversheet comprises a copolymer composition having a mean coefficient of friction of up to 0.45.

Embodiment 84

An article according to embodiment 83, wherein the mean coefficient of friction of the copolymer composition on the outer surface of the second coversheet is at least 0.2.

Embodiment 85

An article according to any one of embodiments 82 to 84, wherein the mean coefficient of friction of the copolymer composition on the outer surface of the second coversheet is up to 0.35.

Embodiment 86

A manually shapeable surgical retractor comprising: a shapeable member comprising a malleable core, wherein the shapeable member comprises a first major surface and a second major surface, wherein the first major surface and the second major surface are on opposite sides of the shapeable member and the malleable core; a first coversheet attached to a first major surface of the shapeable member; and a second coversheet attached to a second major surface of the shapeable member; wherein the surgical retractor comprises a perimeter in the general shape of a rectangle, with one or more tabs extending outward from at least one side of the rectangular, wherein each tab of the one or more tabs occupies less than all of the side from which it extends.

Embodiment 87

A surgical retractor according to embodiment 86, wherein the shapeable member extends into the area defined the one or more tabs.

Embodiment 88

A manually shapeable surgical retractor comprising: a shapeable member comprising a malleable core, wherein the shapeable member comprises a first major surface and a second major surface, wherein the first major surface and the second major surface are on opposite sides of the shapeable member and the malleable core; a first coversheet attached to a first major surface of the shapeable member; and a second coversheet attached to a second major surface of the shapeable member; wherein the surgical retractor comprises non-rectangular shape comprising a central portion and two or more fingers extending outwardly from the central portion, wherein the shapeable member extends into each finger of the two or more fingers.

Embodiment 89

A manually shapeable surgical retractor comprising: a shapeable member comprising a malleable core, wherein the shapeable member comprises a first major surface and a second major surface, wherein the first major surface and the second major surface are on opposite sides of the shapeable member and the malleable core; a first coversheet attached to a first major surface of the shapeable member; and a second coversheet attached to a second major surface of the shapeable member; wherein the first coversheet and the second coversheet define a surgical retractor perimeter having a retractor shape, and wherein the shapeable member located between the first coversheet and the second coversheet comprises a member perimeter defining a member shape that is different than the retractor shape.

Embodiment 90

A manually shapeable surgical retractor comprising: a shapeable member comprising a malleable core, wherein the shapeable member comprises a first major surface and a second major surface, wherein the first major surface and the second major surface are on opposite sides of the shapeable member and the malleable core; a first coversheet attached to a first major surface of the shapeable member; and a second coversheet attached to a second major surface of the shapeable member; wherein the first coversheet and the second coversheet define a surgical retractor perimeter having a retractor shape, and wherein the shapeable member located between the first coversheet and the second coversheet comprises a member perimeter defining a member shape that is the same as the retractor shape.

Embodiment 91

A manually shapeable surgical retractor comprising: a shapeable member comprising a malleable core, wherein the shapeable member comprises a first major surface and a second major surface, wherein the first major surface and the second major surface are on opposite sides of the shapeable member and the malleable core; a first coversheet attached to a first major surface of the shapeable member; and a second coversheet attached to a second major surface of the shapeable member; wherein the first coversheet and the second coversheet define an article perimeter having a generally rectangular shape, and wherein the shapeable member located between the first coversheet and the second coversheet comprises a member perimeter defining a non-rectangular member shape that is different than the generally rectangular shape of the article perimeter.

Embodiment 92

A surgical retractor according to embodiment 91, wherein the non-rectangular member shape comprises a generally rectangular shape comprising one or more tabs extending outward from at least one side of the rectangular, wherein each tab of the one or more tabs occupies less than all of the side from which it extends.

Embodiment 93

A surgical retractor according to any one of embodiments 86 to 92, wherein the shapeable member comprises one or more slits formed through the shapeable member, wherein each slit of the one or more slits extends from an edge of the shapeable member inward toward a center of the shapeable member.

Embodiment 94

A surgical retractor according to any one of embodiments 86 to 93, wherein the first coversheet comprises an outer surface facing away from the malleable core, and wherein the outer surface of the first coversheet comprises a copolymer composition having a mean coefficient of friction of 0.2 to 0.45.

Embodiment 95

A surgical retractor according to embodiment 94, wherein the mean coefficient of friction of the copolymer composition is up to 0.35.

Embodiment 96

A surgical retractor according to any one of embodiments 86 to 95, wherein the second coversheet comprises an outer surface facing away from the malleable core, and wherein the outer surface of the second coversheet comprises a copolymer composition having a mean coefficient of friction of at least 0.2.

Embodiment 97

A surgical retractor according to any one of embodiments 86 to 96, wherein the second coversheet comprises an outer surface facing away from the malleable core, and wherein the outer surface of the second coversheet comprises a copolymer composition having a mean coefficient of friction of up to 0.45.

Embodiment 98

A surgical retractor according to embodiment 97, wherein the mean coefficient of friction of the copolymer composition on the outer surface of the second coversheet is at least 0.2.

Embodiment 99

A surgical retractor according to any one of embodiments 96 to 98, wherein the mean coefficient of friction of the copolymer composition on the outer surface of the second coversheet is up to 0.35.

Embodiment 100

A surgical retractor according to any one of embodiments 86 to 99, wherein the shapeable member comprises a stiffness of 100 N according to a three point bend test.

Embodiment 101

A surgical retractor according to any one of embodiments 86 to 100, wherein the malleable core comprises a metal foil layer.

Embodiment 102

A surgical retractor according to any one of embodiments 86 to 101, wherein the malleable core comprises a pair of metal foil layers.

Embodiment 103

A surgical retractor according to any one of embodiments 86 to 100, wherein the shapeable member comprises: a first structured sheet comprising a first land portion connecting a first plurality of structured elements; a second structured sheet comprising a second land portion connecting a second plurality of structured elements; and a malleable metallic core located between the first structured sheet and the second structured sheet, wherein the malleable metallic core is attached to at least a portion of each of the first structured sheet and the second structured sheet.

Embodiment 104

A surgical retractor according to any one of embodiments 86 to 103, wherein the first coversheet exhibits tensile elongation greater than zero and 1000% or less.

Embodiment 105

A surgical retractor according to any one of embodiments 86 to 104, wherein the first coversheet comprises one or more layers selected from a foam layer, a polymeric film, a nonwoven sheet, a woven sheet, a knitted sheet, a mesh sheet, and a net sheet.

Embodiment 106

A surgical retractor according to any one of embodiments 86 to 105, wherein the first coversheet comprises a compressible layer.

Embodiment 107

A surgical retractor according to embodiment 106, wherein the compressible layer comprises closed cell foam.

Embodiment 108

A surgical retractor according to any one of embodiments 106 to 107, wherein the compressible layer exhibits compression set of 50% or less of an original thickness when tested according to ASTM D3575.

Embodiment 109

A surgical retractor according to any one of embodiments 86 to 108, wherein the second coversheet exhibits tensile elongation greater than zero and 1000% or less.

Embodiment 110

A surgical retractor according to any one of embodiments 86 to 109, wherein the second coversheet comprises one or more layers selected from a foam layer, a polymeric film, a nonwoven sheet, a woven sheet, a knitted sheet, a mesh sheet, and a net sheet.

Embodiment 111

A surgical retractor according to any one of embodiments 86 to 110, wherein the second coversheet comprises a compressible layer.

Embodiment 112

A surgical retractor according to embodiment 111, wherein the compressible layer of the second coversheet comprises closed cell foam.

Embodiment 113

An article according to any one of embodiments 111 to 112, wherein the compressible layer of the second coversheet exhibits compression set of 50% or less of an original thickness when tested according to ASTM D3575.

Embodiment 114

A shapeable article according to any one of embodiments 1 to 85 or a surgical retractor according to any one of embodiments 86-113, wherein the shapeable member comprises a member perimeter, and wherein an edge protector extends about at least a portion of the member perimeter, and wherein at least a portion of the edge protector is located between the first cover sheet and the second cover sheet.

Embodiment 115

A shapeable article or a surgical retractor according to embodiment 114, wherein the edge protector comprises a compressible edge protector.

Embodiment 116

A shapeable article or a surgical retractor according to any one of embodiments 114 to 115, wherein the edge protector extends about only a portion of the member perimeter of the shapeable member.

Embodiment 117

A shapeable article or a surgical retractor according to any one of embodiments 114 to 115, wherein the edge protector extends about the entire member perimeter of the shapeable member.

Embodiment 118

A kit comprising a lap sponge, a surgical retractor comprising the manually shapeable article according to any one of embodiments 1 to 85 and 114 to 117 or a surgical retractor according to any one of embodiments 86 to 113 or 114 to 117, and a frangible sealed package containing the lap sponge and the surgical retractor.

Embodiment 119

A method of manufacturing manually a shapeable article according to any one of embodiments 1 to 85 and 114 to 117 or a surgical retractor according to any one of embodiments 86 to 113 or 114 to 117.

It should be understood that although exemplary articles, kits, and methods are described herein as "comprising" one or more components, features or steps, the methods may "comprise," "consists of," or "consist essentially of" any of the above-described components and/or features and/or steps. Consequently, where the present invention, or a portion thereof, has been described with an open-ended term such as "comprising," it should be readily understood that (unless otherwise stated) the description of the present invention, or the portion thereof, should also be interpreted to describe the present invention, or a portion thereof, using the terms "consisting essentially of" or "consisting of" or variations thereof as discussed below.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, an article, kit, or method that "comprises" a list of elements (e.g., components or features or steps) is not necessarily limited to only those elements (or components or features or steps), but may include other elements (or components or features or steps) not expressly listed or inherent to the method.

As used herein, the singular forms "a," "an," and "the" include plural referents unless the context clearly dictates otherwise. Thus, for example, reference to "a" or "the" component may include one or more of the components and equivalents thereof known to those skilled in the art. Further, the term "and/or" means one or all of the listed elements or a combination of any two or more of the listed elements.

Further, the term "comprises" and variations thereof do not have a limiting meaning where these terms appear in the accompanying description. Moreover, "a," "an," "the," "at least one," and "one or more" are used interchangeably herein.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define an article, kit, or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of". Further, it should be understood that the herein-described articles, kits, or methods may comprise, consist essentially of, or consist of any of the herein-described components and features, as shown in the figures with or without any additional feature(s) not shown in the figures. In other words, in some embodiments, the articles, kits, or methods of the present invention may have any additional feature that is not specifically shown in the figures. In some embodiments, the articles, kits, or methods of the present invention do not have any additional features other than those (i.e., some or all) shown in the figures, and such additional features, not shown in the figures, are specifically excluded from the articles, kits, or methods.

The complete disclosure of the patents, patent documents, and publications identified herein are incorporated by reference in their entirety as if each were individually incorporated. To the extent there is a conflict or discrepancy between this document and the disclosure in any such incorporated document, this document will control.

From the above disclosure of the general principles of the present invention and the preceding detailed description, those skilled in this art will readily comprehend the various modifications, re-arrangements and substitutions to which the present invention is susceptible, as well as the various advantages and benefits the present invention may provide. Therefore, the scope of the invention should be limited only by the following claims and equivalents thereof. In addition, it is understood to be within the scope of the present invention that the disclosed and claimed articles and methods may be useful in applications other than surgical procedures. Therefore, the scope of the invention may be broadened to include the use of the claimed and disclosed methods for such other applications.

The invention claimed is:

1. A manually shapeable article comprising:
   a shapeable member comprising:
      a first sheet comprising a first major surface and a second major surface, wherein the first major surface and the second major surface are on opposite sides of the first sheet, wherein the first sheet further comprises a land portion extending between and connecting a plurality of structured elements, wherein each structured element of the plurality of structured elements comprises a protrusion extending from the land portion on the first major surface of the first sheet;
      a second sheet comprising a first major surface and a second major surface, wherein the first major surface and the second major surface are on opposite sides of the second sheet, wherein the second sheet further comprises a land portion extending between and connecting a plurality of structured elements, wherein each structured element of the plurality of structured elements comprises a protrusion extending from the land portion on the first major surface of the second sheet;
      wherein the first sheet is attached to the second sheet such that the second major surface of the first sheet faces the first or second major surface of the second sheet;
   a first coversheet attached to a first major surface of the shapeable member; and
   a second coversheet attached to a second major surface of the shapeable member, wherein one or both of the first coversheet and the second coversheet comprises a compressible layer, the compressible layer comprises closed cell foam.

2. An article according to claim 1, wherein each structured element of the first sheet comprises a depression on the second major surface that corresponds to the protrusion extending from the first major surface of the first sheet.

3. An article according to claim 1, wherein each structured element of the second sheet comprises a depression on the second major surface that corresponds to each protrusion extending from the first major surface of the second sheet.

4. An article according to claim 1, wherein the land portion between the plurality of structured elements on the first sheet is attached to the land portion between the plurality of structured elements on the second sheet.

5. An article according to claim 1, wherein one or both of the first sheet and the second sheet comprises a metal foil.

6. An article according to claim 1, wherein one or both of the first sheet and the second sheet comprises a polymeric sheet comprising the land portions and the plurality of structured elements.

7. An article according to claim 1, wherein one or both of the first coversheet and the second coversheet exhibits tensile elongation greater than zero and 1000% or less.

8. An article according to claim 1, wherein one or both of the first coversheet and the second coversheet comprises one or more layers selected from a foam layer, a polymeric film, a nonwoven sheet, a woven sheet, a knitted sheet, a mesh sheet, and a net sheet.

9. An article according to claim 1, wherein the compressible layer exhibits compression set of 50% or less of an original thickness when tested according to ASTM D3575.

10. An article according to claim 1, wherein the shapeable member comprises one or more slits formed through the shapeable member, wherein each slit of the one or more slits extends from an edge of the shapeable member inward toward a center of the shapeable member.

11. An article according to claim 1, wherein the shapeable member comprises a window opening formed therein, wherein the shapeable member forms a frame around the window opening.

12. An article according to claim 11, wherein the first coversheet and the second coversheet extend over the window opening formed in the shapeable member.

13. An article according to claim 1, wherein the article comprises a stiffness of 100 N or less according to a three-point bend test.

14. An article according to claim 1, wherein one or both of the first coversheet and the second coversheet comprises an outer surface facing away from the shapeable member, and wherein the outer surface comprises a copolymer composition having a mean coefficient of friction of at least 0.2.

15. An article according to claim 1, wherein one or both of the first coversheet and the second coversheet comprises an outer surface facing away from the shapeable member, and wherein the outer surface comprises a copolymer composition having a mean coefficient of friction of up to 0.45.

* * * * *